(12) United States Patent
Zhamu et al.

(10) Patent No.: US 11,258,101 B2
(45) Date of Patent: Feb. 22, 2022

(54) NON-FLAMMABLE ELECTROLYTE CONTAINING LIQUEFIED GAS AND LITHIUM SECONDARY BATTERIES CONTAINING SAME

(71) Applicant: Nanotek Instruments, Inc., Dayton, OH (US)

(72) Inventors: Aruna Zhamu, Springboro, OH (US); Bor Z. Jang, Centerville, OH (US)

(73) Assignee: Global Graphene Group, Inc., Dayton, OH (US)

( * ) Notice: Subject to any disclaimer, the term of this patent is extended or adjusted under 35 U.S.C. 154(b) by 0 days.

(21) Appl. No.: 15/633,369

(22) Filed: Jun. 26, 2017

(65) Prior Publication Data

US 2018/0375156 A1    Dec. 27, 2018

(51) Int. Cl.
*H01M 10/0569* (2010.01)
*H01M 4/134* (2010.01)
(Continued)

(52) U.S. Cl.
CPC ........... *H01M 10/0569* (2013.01); *C07C 9/04* (2013.01); *C07C 11/04* (2013.01); *C07C 19/00* (2013.01); *C07C 19/03* (2013.01); *C07C 19/043* (2013.01); *C07C 19/08* (2013.01); *C07C 21/00* (2013.01); *C07C 21/04* (2013.01); *C07C 21/18* (2013.01); *H01M 4/134* (2013.01);
(Continued)

(58) Field of Classification Search
CPC ......... H01M 10/0525; H01M 10/0569; H01M 4/134; C07C 19/00; C07C 21/00
See application file for complete search history.

(56) References Cited

U.S. PATENT DOCUMENTS

| 2,798,878 A | 7/1957 | Hummers |
| 5,532,077 A | 7/1996 | Chu |

(Continued)

OTHER PUBLICATIONS

C. S. Rustomji, et al., "Liquefied gas electrolytes for electrochemical energy storage devices," Science 10.1126/science.aal4263 (2017).
(Continued)

*Primary Examiner* — Karie O'Neill Apicella

(57) ABSTRACT

A rechargeable lithium cell comprising a cathode, an anode, an optional ion-permeable membrane disposed between the anode and the cathode, a non-flammable salt-retained liquefied gas electrolyte in contact with the cathode and the anode, wherein the electrolyte contains a lithium salt dissolved in or mixed with a liquefied gas solvent having a lithium salt concentration greater than 1.0 M so that the electrolyte exhibits a vapor pressure less than 1 kPa when measured at 20° C., a vapor pressure less than 60% of the vapor pressure of the liquefied gas solvent alone, a flash point at least 20 degrees Celsius higher than a flash point of the liquefied gas solvent alone, a flash point higher than 150° C., or no flash point, wherein the liquefied gas solvent is selected from methane, fluoromethane, difluoromethane, chloromethane, dichloromethane, ethane, fluoroethane, difluoroethane, tetrafluoroethane, chloroethane, dichloroethane, tetrachloroethane, propane, fluoropropane, chloropropane, ethylene, fluoroethylene, chloroethylene, or a combination thereof.

41 Claims, 10 Drawing Sheets

(51) Int. Cl.

| | |
|---|---|
| *H01M 10/0525* | (2010.01) |
| *C07C 21/00* | (2006.01) |
| *C07C 19/00* | (2006.01) |
| *C07C 11/04* | (2006.01) |
| *C07C 19/043* | (2006.01) |
| *C07C 21/18* | (2006.01) |
| *C07C 19/03* | (2006.01) |
| *C07C 9/04* | (2006.01) |
| *C07C 21/04* | (2006.01) |
| *H01M 10/42* | (2006.01) |
| *H01M 10/0568* | (2010.01) |
| *C07C 19/08* | (2006.01) |

(52) U.S. Cl.
CPC ... *H01M 10/0525* (2013.01); *H01M 10/0568* (2013.01); *H01M 10/4235* (2013.01); *H01M 2300/0031* (2013.01); *H01M 2300/0034* (2013.01); *H01M 2300/0037* (2013.01)

(56) References Cited

U.S. PATENT DOCUMENTS

| | | | |
|---|---|---|---|
| 6,013,394 | A | 1/2000 | Gan et al. |
| 9,368,831 | B2 | 6/2016 | He et al. |
| 9,601,803 | B2 | 3/2017 | He et al. |
| 10,608,284 | B2 * | 3/2020 | Rustomji .......... H01M 10/0525 |
| 2005/0271574 | A1 | 12/2005 | Jang et al. |
| 2012/0183865 | A1 | 7/2012 | Deguchi |
| 2013/0164604 | A1 | 6/2013 | Matsumoto et al. |
| 2015/0024121 | A1* | 1/2015 | He .................... H01M 10/0566 427/121 |
| 2015/0044556 | A1 | 2/2015 | Wang et al. |
| 2015/0064575 | A1* | 3/2015 | He .................... H01M 10/0568 429/300 |
| 2016/0261005 | A1* | 9/2016 | Rustomji ............ H01M 10/052 |
| 2017/0271653 | A1 | 9/2017 | Yamauchi et al. |
| 2018/0183052 | A1 | 6/2018 | Zhamu et al. |

OTHER PUBLICATIONS

PCT/US18/31525 International Search Report and Written Opinion dated Jul. 23, 2018, 10 pages.

Fang et al., "A novel mixture of diethylene glycol diethylether and non-flammable methyl-nonafluorobutyl ether as a safe electrolyte for lithium ion batteries" Journal of Materials Chemistry A. (2015) vol. 3, pp. 21159-21166.

PCT/US17/38262, International Search Report and Written Opinion dated Aug. 23, 2017, 9 pages.

U.S. Appl. No. 15/468,080 Final Office Action dated Feb. 24, 2020, 11 pages.

U.S. Appl. No. 15/468,080 Final Office Action dated Jan. 12, 2021, 7 pages.

U.S. Appl. No. 15/468,080 Nonfinal Office Action dated Oct. 9, 2019, 11 pages.

U.S. Appl. No. 15/468,080 Nonfinal Office Action dated Aug. 24, 2020, 7 pages.

U.S. Appl. No. 15/468,080 Final Office Action dated Aug. 25, 2021; 10 pages.

U.S. Appl. No. 15/468,080 Nonfinal Office Action dated Apr. 19, 2021, 8 pages.

* cited by examiner

NON-FLAMMABLE ELECTROLYTE CONTAINING LIQUEFIED GAS AND LITHIUM SECONDARY BATTERIES CONTAINING SAME

FIELD OF THE INVENTION

The present invention provides a non-flammable electrolyte composition comprising a liquefied gas and a secondary or rechargeable lithium battery containing such an electrolyte composition.

BACKGROUND

Rechargeable lithium-ion (Li-ion), lithium metal, lithium-sulfur, and Li metal-air batteries are considered promising power sources for electric vehicle (EV), hybrid electric vehicle (HEV), and portable electronic devices, such as lap-top computers and mobile phones. Lithium as a metal element has the highest lithium storage capacity (3,861 mAh/g) compared to any other metal or metal-intercalated compound as an anode active material (except $Li_{4.4}Si$, which has a specific capacity of 4,200 mAh/g). Hence, in general, Li metal batteries (having a lithium metal anode) have a significantly higher energy density than lithium-ion batteries (having a graphite anode).

Historically, rechargeable lithium metal batteries were produced using non-lithiated compounds having relatively high specific capacities, such as $TiS_2$, $MoS_2$, $MnO_2$, $CoO_2$, and $V_2O_5$, as the cathode active materials, which were coupled with a lithium metal anode. When the battery was discharged, lithium ions were transferred from the lithium metal anode to the cathode through the electrolyte and the cathode became lithiated. Unfortunately, upon repeated charges and discharges, the lithium metal resulted in the formation of dendrites at the anode that ultimately caused internal shorting, thermal runaway, and explosion. As a result of a series of accidents associated with this problem, the production of these types of secondary batteries was stopped in the early 1990's giving ways to lithium-ion batteries.

Even now, cycling stability and safety concerns remain the primary factors preventing the further commercialization of Li metal batteries (e.g. Lithium-sulfur and Lithium-transition metal oxide cells) for EV, HEV, and microelectronic device applications. Again, cycling stability and safety issues of lithium metal rechargeable batteries are primarily related to the high tendency for Li metal to form dendrite structures during repeated charge-discharge cycles or overcharges, leading to internal electrical shorting and thermal runaway. This thermal runaway or even explosion is caused by the organic liquid solvents used in the electrolyte (e.g. carbonate and ether families of solvents), which are unfortunately highly volatile and flammable.

Many attempts have been made to address the dendrite and thermal runaway issues. However, despite these earlier efforts, no rechargeable Li metal batteries have succeeded in the market place. This is likely due to the notion that these prior art approaches still have major deficiencies. For instance, in several cases, the anode or electrolyte structures designed for prevention of dendrites are too complex. In others, the materials are too costly or the processes for making these materials are too laborious or difficult. In most of the lithium metal cells and lithium-ion cells, the electrolyte solvents are flammable. An urgent need exists for a simpler, more cost-effective, and easier to implement approach to preventing Li metal dendrite-induced internal short circuit and thermal runaway problems in Li metal batteries and other rechargeable batteries.

Parallel to these efforts and prompted by the aforementioned concerns over the safety of earlier lithium metal secondary batteries led to the development of lithium-ion secondary batteries, in which pure lithium metal sheet or film was replaced by carbonaceous materials (e.g. natural graphite particles) as the anode active material. The carbonaceous material absorbs lithium (through intercalation of lithium ions or atoms between graphene planes, for instance) and desorbs lithium ions during the re-charge and discharge phases, respectively, of the lithium-ion battery operation. The carbonaceous material may comprise primarily graphite that can be intercalated with lithium and the resulting graphite intercalation compound may be expressed as $Li_xC_6$, where x is typically less than 1.

Although lithium-ion (Li-ion) batteries are promising energy storage devices for electric drive vehicles, state-of-the-art Li-ion batteries have yet to meet the cost, safety, and performance targets. Li-ion cells typically use a lithium transition-metal oxide or phosphate as a positive electrode (cathode) that de/re-intercalates $Li^+$ at a high potential with respect to the carbon negative electrode (anode). The specific capacity of lithium transition-metal oxide or phosphate based cathode active material is typically in the range of 140-170 mAh/g. As a result, the specific energy of commercially available Li-ion cells is typically in the range of 120-220 Wh/kg, most typically 150-180 Wh/kg. These specific energy values are two to three times lower than what would be required for battery-powered electric vehicles to be widely accepted.

Furthermore, the same flammable solvents previously used for lithium metal secondary batteries are also used in most of the lithium-ion batteries. Despite the notion that there is significantly reduced propensity of forming dendrites in a lithium-ion cell (relative to a lithium metal cell), the lithium-ion cell has its own intrinsic safety issue. For instance, the transition metal elements in the lithium metal oxide cathode are highly active catalysts that can promote and accelerate the decomposition of organic solvents, causing thermal runaway or explosion initiation to occur at a relatively low electrolyte temperature (e.g. <200° C., as opposed to normally 400° C. without the catalytic effect).

A recent attempt was made to use a liquefied gas as a solvent to extend the lithium-ion battery operating temperature to as low as −60° C. and to reduce the tendency to form lithium dendrite [C. S. Rustomji, et al., "Liquefied gas electrolytes for electrochemical energy storage devices," Science 10.1126/science.aal4263 (2017)]. However, the liquefied gases investigated can only dissolve a lithium salt up to a concentration of 0.75 M (mostly lower than 0.1 M and more typically as low as 0.02 M), which are not conducive to high lithium storage capacity of the lithium-ion battery. Most significantly, methane-, ethane-, and propane-based liquefied gases are known to be used for their flammability (for burning), which is totally opposite to the need for a non-flammable battery electrolyte. Further, in order for these gases to be liquefied, they must be submitted to a high gas pressure, at least in a saturated vapor pressure state. The resulting battery is prone to gas leakage and easy ignition.

Ionic liquids (ILs) are a new class of purely ionic, salt-like materials that are liquid at unusually low temperatures. The official definition of ILs uses the boiling point of water as a point of reference: "Ionic liquids are ionic compounds which are liquid below 100° C.". A particularly useful and scientifically interesting class of ILs is the room temperature ionic liquid (RTIL), which refers to the salts that are liquid at room temperature or below. RTILs are also referred to as organic liquid salts or organic molten salts. An accepted definition of an RTIL is any salt that has a melting temperature lower than ambient temperature.

Although ILs were suggested as a potential electrolyte for rechargeable lithium batteries due to their non-flammability, conventional ionic liquid compositions have not exhibited satisfactory performance when used as an electrolyte likely due to several inherent drawbacks: (a) ILs have relatively high viscosity at room or lower temperatures; thus being considered as not amenable to lithium ion transport; (b) For Li—S cell uses, ILs are capable of dissolving lithium polysulfides at the cathode and allowing the dissolved species to migrate to the anode (i.e., the shuttle effect remains severe); and (c) For lithium metal secondary cells, most of the ILs strongly react with lithium metal at the anode, continuing to consume Li and deplete the electrolyte itself during repeated charges and discharges. These factors lead to relatively poor specific capacity (particularly under high current or high charge/discharge rate conditions, hence lower power density), low specific energy density, rapid capacity decay and poor cycle life. Furthermore, ILs remain extremely expensive. Consequently, as of today, no commercially available lithium battery makes use of an ionic liquid as the primary electrolyte component.

With the rapid development of hybrid (HEV), plug-in hybrid electric vehicles (HEV), and all-battery electric vehicles (EV), there is an urgent need for anode and cathode materials and electrolytes that provide a rechargeable battery with a significantly higher specific energy, higher energy density, higher rate capability, long cycle life, and safety. One of the most promising energy storage devices is the lithium-sulfur (Li—S) cell since the theoretical capacity of Li is 3,861 mAh/g and that of S is 1,675 mAh/g. In its simplest form, a Li—S cell consists of elemental sulfur as the positive electrode and lithium as the negative electrode. The lithium-sulfur cell operates with a redox couple, described by the reaction $S_8 + 16Li \leftrightarrow 8Li_2S$ that lies near 2.2 V with respect to $Li^+/Li^\circ$. This electrochemical potential is approximately ⅔ of that exhibited by conventional positive electrodes. However, this shortcoming is offset by the very high theoretical capacities of both Li and S. Thus, compared with conventional intercalation-based Li-ion batteries, Li—S cells have the opportunity to provide a significantly higher energy density (a product of capacity and voltage). Values can approach 2,500 Wh/kg or 2,800 Wh/l based on the combined Li and S weight or volume (not based on the total cell weight or volume), respectively, assuming complete reaction to $Li_2S$. With a proper cell design, a cell-level specific energy of 1,200 Wh/kg (of cell weight) and cell-level energy density of 1,400 Wh/l (of cell volume) should be achievable. However, the current Li-sulfur products of industry leaders in sulfur cathode technology have a maximum cell specific energy of 400 Wh/kg (based on the total cell weight), far less than what could be obtained in real practice.

In summary, despite its considerable advantages, the rechargeable lithium metal cell in general and the Li—S cell and the Li-air cell in particular are plagued with several major technical problems that have hindered its widespread commercialization:

(1) Conventional lithium metal secondary cells (e.g., rechargeable Li metal cells, Li—S cells, and Li-Air cells) still have dendrite formation and related internal shorting and thermal runaway issues. Also, conventional Li-ion cells still make use of significant amounts of flammable liquids (e.g. propylene carbonate, ethylene carbonate, 1,3-dioxolane, etc) as the primary electrolyte solvent, risking danger of explosion;

(2) The Li—S cell tends to exhibit significant capacity degradation during discharge-charge cycling. This is mainly due to the high solubility of the lithium polysulfide anions formed as reaction intermediates during both discharge and charge processes in the polar organic solvents used in electrolytes. During cycling, the lithium polysulfide anions can migrate through the separator and electrolyte to the Li negative electrode whereupon they are reduced to solid precipitates ($Li_2S_2$ and/or $Li_2S$), causing active mass loss. In addition, the solid product that precipitates on the surface of the positive electrode during discharge can become electrochemically irreversible, which also contributes to active mass loss.

(3) More generally speaking, a significant drawback with cells containing cathodes comprising elemental sulfur, organosulfur and carbon-sulfur materials relates to the dissolution and excessive out-diffusion of soluble sulfides, polysulfides, organo-sulfides, carbon-sulfides and/or carbon-polysulfides (hereinafter referred to as anionic reduction products) from the cathode into the rest of the cell. This phenomenon is commonly referred to as the Shuttle Effect. This process leads to several problems: high self-discharge rates, loss of cathode capacity, corrosion of current collectors and electrical leads leading to loss of electrical contact to active cell components, fouling of the anode surface giving rise to malfunction of the anode, and clogging of the pores in the cell membrane separator which leads to loss of ion transport and large increases in internal resistance in the cell.

In response to these challenges, new electrolytes, protective films for the lithium anode, and solid electrolytes have been developed. Some interesting cathode developments have been reported recently to contain lithium polysulfides; but, their performance still fall short of what is required for practical applications. Despite the various approaches proposed for the fabrication of high energy density rechargeable cells containing elemental sulfur, organo-sulfur and carbon-sulfur cathode materials, or derivatives and combinations thereof, there remains a need for materials and cell designs that (a) retard the out-diffusion of anionic reduction products, from the cathode compartments into other components in these cells, (b) improve the battery safety, and (c) provide rechargeable cells with high capacities over a large number of cycles.

Again, lithium metal (including pure lithium, alloys of lithium with other metal elements, or lithium-containing compounds) still provides the highest anode specific capacity as compared to essentially all other anode active materials (except pure silicon, but silicon has pulverization issues). Lithium metal would be an ideal anode material in a lithium-sulfur secondary battery if dendrite related issues, such as fire and explosion danger, could be addressed. In addition, there are several non-lithium anode active materials that exhibit high specific lithium-storing capacities (e.g., Si, Sn, $SnO_2$, and Ge as an anode active material) in a lithium ion battery wherein lithium is inserted into the lattice sites of Si, Sn, $SnO_2$, or Ge in a charged state. These potentially useful anode materials have been largely ignored in the prior art Li—S cells.

Hence, a general object of the present invention is to provide a safe, non-flammable quasi-electrolyte electrolyte system for a rechargeable lithium cell that is compatible with existing battery production facilities. In addition, the battery exhibits a high energy density, high power density, long cycle life, and no danger of explosion due to the. This lithium cell includes the lithium metal secondary cell (e.g. Li—S, Li—TiS$_2$, Li—MoS$_2$, Li—VO$_2$, and Li-air, just to name a few), lithium-ion cell (e.g. graphite-LiMn$_2$O$_4$, Si—Li$_x$Ni$_y$Mn$_z$O$_2$, etc.), Li-ion sulfur cell (e.g. prelithiated Si—S cell), and hybrid lithium cell (wherein at least one electrode operates on lithium insertion or intercalation).

A specific object of the present invention is to provide a rechargeable Li—S battery that exhibits an exceptionally high specific energy or high energy density and a high level of safety. One specific technical goal of the present invention is to provide a safe Li metal-sulfur or Li ion-sulfur cell having a long cycle life and a cell specific energy greater than 400 Wh/Kg, preferably greater than 500 Wh/Kg, and more preferably greater than 600 Wh/Kg (all based on the total cell weight).

Another specific object of the present invention is to provide a safe lithium-sulfur cell that exhibits a high specific capacity (higher than 1,200 mAh/g based on the sulfur weight, or higher than 1,000 mAh/g based on the cathode composite weight, including sulfur, conducting additive and conductive substrate, and binder weights combined, but excluding the weight of cathode current collector). The specific capacity is preferably higher than 1,400 mAh/g based on the sulfur weight alone or higher than 1,200 mAh/g based on the cathode composite weight. This must be accompanied by a high specific energy, good resistance to dendrite formation, good resistance to thermal runaway, no possibility of an explosion, and a long and stable cycle life.

It may be noted that in most of the open literature reports (scientific papers) on Li—S cells, scientists choose to express the cathode specific capacity based on the sulfur weight or lithium polysulfide weight alone (not on the total cathode composite weight), but unfortunately a large proportion of non-active materials (those not capable of storing lithium, such as conductive additive and binder) is typically used in their Li—S cells. Similarly, for lithium-vanadium oxide cells, scientists also tend to report the cathode specific capacity based on the vanadium oxide weight only. For practical usage purposes, it is more meaningful to use the cathode composite weight-based capacity value.

A specific object of the present invention is to provide a rechargeable lithium-sulfur cell based on rational materials and battery designs that overcome or significantly reduce the following issues commonly associated with conventional Li—S cells: (a) dendrite formation (internal shorting); (b) extremely low electric and ionic conductivities of sulfur, requiring large proportion (typically 30-55%) of non-active conductive fillers and having significant proportion of non-accessible or non-reachable sulfur or lithium polysulfides); (c) dissolution of lithium polysulfide in electrolyte and migration of dissolved lithium polysulfides from the cathode to the anode (which irreversibly react with lithium at the anode), resulting in active material loss and capacity decay (the shuttle effect); and (d) short cycle life.

Another object of the present invention is to provide a simple, cost-effective, and easy-to-implement approach to preventing potential Li metal dendrite-induced internal short circuit and thermal runaway problems in various Li metal and Li-ion batteries.

SUMMARY OF THE INVENTION

As a first embodiment, the present invention provides a rechargeable lithium battery, including a lithium metal secondary cell, a lithium-ion cell, a lithium-sulfur cell, a lithium-ion sulfur cell, a lithium-selenium cell, or a lithium-air cell. This battery features a non-flammable, safe, and high-performing electrolyte.

The invented rechargeable lithium cell comprises a cathode having a cathode active material, an anode having an anode active material, an optional ion-permeable membrane disposed between the anode and the cathode, a non-flammable salt-retained liquefied gas electrolyte in contact with the cathode and the anode, wherein the electrolyte contains a lithium salt dissolved in or mixed with a liquefied gas solvent having a lithium salt concentration greater than 1.0 M (typically from 1 M to 14 M) so that the electrolyte exhibits a vapor pressure less than 1 kPa (preferably less than 0.1 kPa and more preferably less than 0.01 kPa) when measured at 20° C., a vapor pressure less than 60% of the vapor pressure of the liquefied gas solvent alone, a flash point at least 20 degrees Celsius higher than a flash point of the liquefied gas solvent alone, a flash point higher than 150° C., or no flash point, wherein the liquefied gas solvent is selected from methane, fluoromethane, difluoromethane, chloromethane, dichloromethane, ethane, fluoroethane, difluoroethane, tetrafluoroethane, chloroethane, dichloroethane, tetrachloroethane, propane, fluoropropane, chloropropane, ethylene, fluoroethylene, chloroethylene, or a combination thereof.

In certain embodiments, the lithium salt concentration is from 1.5 M to 10 M. In certain preferred embodiments, the concentration is from 2.0 M to 5.0 M.

It may be noted that natural gases and their modified versions (e.g. methane, fluoromethane, difluoromethane, chloromethane, dichloromethane, ethane, fluoroethane, difluoroethane (e.g. 1,1-Dichloro-1-fluoroethane), tetrafluoroethane, chloroethane, dichloroethane, tetrachloroethane, propane, fluoropropane, chloropropane, ethylene, fluoroethylene, and chloroethylene, etc.), even in a liquefied state, are not capable of dissolving a lithium salt up to a concentration of 0.75 M; typically <0.5 M, more typically <0.1 M, and most typically approximately 0.02 M. We have found several innovative ways of achieving a lithium salt concentration from 0.75 M to 14 M (or higher, if so desired).

Further, we have surprisingly discovered that the flammability of any liquefied gas solvent can be effectively suppressed provided that a sufficiently high amount of a lithium salt (e.g. from 1.5 M to 14 M; preferably >2.5 M) is added to and dissolved in a liquefied gas to form a solid-like or quasi-solid electrolyte.

In general, such a quasi-solid electrolyte exhibits a vapor pressure less than 1.0 kPa (when measured at 20° C.) and less than 0.1 kPa (when measured at 100° C.). More typically, the vapor pressure is less than 0.1 kPa and further more typically <0.01 kPa (when measured at 20° C.). In many cases, the vapor molecules are practically too few to be detected when the lithium salt concentration is sufficiently high. The high solubility of the lithium salt in an otherwise highly volatile solvent has effectively prevented the flammable gas molecules from initiating a flame even at an extremely high temperature (e.g. using a torch). The flash point of the quasi-solid electrolyte is typically at least 20 degrees (often >50 degrees) higher than the flash point of the neat liquefied gas solvent alone. In most of the cases, either the flash point is higher than 150° C. or no flash point can be detected. The electrolyte just would not catch on fire or get ignited. Any accidentally initiated flame does not sustain for longer than a few seconds. This is a highly significant discovery, considering the notion that fire and explosion concern has been a major impediment to widespread acceptance of battery-powered electric vehicles. This new technology could potentially reshape the landscape of EV industry.

Another surprising element of the present invention is the notion that we are able to dissolve a high concentration of a lithium salt in a liquefied gas solvent to form an electrolyte suitable for use in a rechargeable lithium battery. This concentration is typically greater than a lithium salt molecular ratio (molecular fraction) of approximately >0.12 (corresponding to approximately >1.5 M or mole/liter), more typically >0.15 (approximately >1.9 M), can be >0.2 (>2.5 M), >0.3 (>3.75 M) and even >0.4 (>5 M). The equivalency between molecular fraction figure and molar concentration figure (mole/liter) varies from one salt/solvent combination to another.

In the instant invention, with a liquefied gas selected and added, the concentration is typically and preferably from 1.5 M to 7.0 M, still more typically and preferably from 2.0 M to 5.0M, and most preferably from 2.5 M to 3.5 M. Such a high concentration of lithium salt in a liquefied gas solvent has not been thought possible or desirable. Indeed, in general, it has not been possible to achieve a lithium salt concentration in any liquefied gas solvent higher than 0.75 M and, even in organic solvents, 1 M is a standard concentration in a lithium-ion battery. The maximum lithium salt concentration in a liquefied gas is significantly lower than that in an organic solvent.

After an extensive and in-depth study, we came to further discover that the apparent solubility of a lithium salt could be significantly increased by several methods. One method includes (a) using a highly volatile co-solvent to increase the amount of lithium salt dissolved in a mixture of a liquefied gas and a volatile organic co-solvent first and then (b) partially or totally removing this volatile co-solvent once the dissolution procedure is completed. Quite unexpectedly, the removal of this co-solvent typically did not lead to precipitation or crystallization of the lithium salt out of the solution even though the solution would have been in a highly supersaturated state. This novel and unique approach appears to have produced a material state wherein most of the solvent molecules are retained or captured by lithium salt ions that are not volatile. Hence, very few solvent molecules are able to escape into the vapor phase. Consequently, very few volatile gas molecules can be present to initiate or sustain a flame. This has not been suggested as technically possible or viable in any previous report.

Another method involves dissolving a lithium salt in a liquefied gas under a high pressure environment (at least equal to the saturation vapor pressure, but typically 1 to 10 atm at 20° C.) to a maximum salt concentration $C_1$ and then removing (vaporizing) the natural gas at a higher temperature and/or a lower pressure (and preferably under a pumping operation to pump out a desired amount of the previously liquefied gas) to achieve a significantly higher salt concentration $C_2$ ($C_2 > C_1$). This action also puts the lithium salt in a supersaturated state without crystallization.

It may be noted that a good scientist in the field of chemistry or materials science would have anticipated that such a high salt concentration would make the electrolyte behave like a solid with an extremely high viscosity and, hence, this electrolyte would not be amenable to fast diffusion of lithium ions therein. Consequently, the scientist would have expected that a lithium battery containing such a solid-like electrolyte would not and could not exhibit a high capacity at a high charge-discharge rate or under a high current density condition (i.e. the battery should have a poor rate capability). Contrary to these expectations, all the lithium cells containing such a liquefied gas-based quasi-solid electrolyte deliver surprisingly high energy density and high power density for a long cycle life. The quasi-solid electrolytes as herein disclosed are conducive to facile lithium ion transport. This surprising observation is manifested by a high lithium ion transference number (TN), to be further explained in a later section of this specification. We have found that the liquefied gas-based quasi-solid electrolytes provide a TN greater than 0.3 (typically in the range of 0.4-0.8), in contrast to the typical values of 0.1-0.2 in all lower concentration electrolytes (e.g. <1.5 M) used in all current Li-ion and Li—S cells.

The rechargeable lithium cell preferably contains a quasi-solid electrolyte having a lithium ion transference number greater than 0.4, preferably and typically greater than 0.6, and most preferably and typically greater than 0.7. It may be noted that the lithium ion transference number of an electrolyte (given the same type and concentration of lithium salt in the same solvent) can vary from a battery type to another; e.g. from a lithium metal cell (where the anode is Li metal) to a lithium-ion cell (where the anode is Sn). The total amount of lithium available for moving back and forth between the anode and the cathode is an important factor that can dictate this transference number.

The lithium salt may be preferably selected from lithium perchlorate ($LiClO_4$), lithium hexafluorophosphate ($LiPF_6$), lithium borofluoride ($LiBF_4$), lithium hexafluoroarsenide ($LiAsF_6$), lithium trifluoro-metasulfonate ($LiCF_3SO_3$), bis-trifluoromethyl sulfonylimide lithium ($LiN(CF_3SO_2)_2$), lithium bis(oxalato)borate (LiBOB), lithium oxalyldifluoroborate ($LiBF_2C_2O_4$), lithium oxalyldifluoroborate ($LiBF_2C_2O_4$), lithium nitrate ($LiNO_3$), Li-Fluoroalkyl-Phosphates ($LiPF_3(CF_2CF_3)_3$), lithium bisperfluoro-ethysulfonylimide (LiBETI), lithium bis(trifluoromethanesulphonyl) imide, lithium bis(fluorosulphonyl)imide, lithium trifluoromethanesulfonimide (LiTFSI), an ionic liquid lithium salt, or a combination thereof. Although not preferred, the lithium salt may be selected from LiOH, $Li_2CO_3$, LiF, LiCl, LiI, LiBr, $Li_2SO_4$, etc.

In a preferred rechargeable lithium cell, the cathode active material may be selected from a metal oxide, a metal oxide-free inorganic material, an organic material, a polymeric material, sulfur, lithium polysulfide, selenium, or a combination thereof. The metal oxide-free inorganic material may be selected from a transition metal fluoride, a transition metal chloride, a transition metal dichalcogenide, a transition metal trichalcogenide, or a combination thereof. In a particularly useful embodiment, the cathode active material is selected from $FeF_3$, $FeCl_3$, $CuCl_2$, $TiS_2$, $TaS_2$, $MoS_2$, $NbSe_3$, $MnO_2$, $CoO_2$, an iron oxide, a vanadium oxide, or a combination thereof, if the anode contains lithium metal as the anode active material. The vanadium oxide may be preferably selected from the group consisting of $VO_2$, $Li_xVO_2$, $V_2O_5$, $Li_xV_2O_5$, $V_3O_8$, $Li_xV_3O_8$, $Li_xV_3O_7$, $V_4O_9$, $Li_xV_4O_9$, $V_6O_{13}$, $Li_xV_6O_{13}$, their doped versions, their derivatives, and combinations thereof, wherein $0.1 < x < 5$.

In a rechargeable lithium cell (e.g., the lithium-ion battery cell), the cathode active material may be selected to contain a layered compound $LiMO_2$, spinel compound $LiM_2O_4$, olivine compound $LiMPO_4$, silicate compound $Li_2MSiO_4$, Tavorite compound $LiMPO_4F$, borate compound $LiMBO_3$, or a combination thereof, wherein M is a transition metal or a mixture of multiple transition metals.

In a preferred lithium metal secondary cell, the cathode active material preferably contains an inorganic material selected from: (a) bismuth selenide or bismuth telluride, (b)

transition metal dichalcogenide or trichalcogenide, (c) sulfide, selenide, or telluride of niobium, zirconium, molybdenum, hafnium, tantalum, tungsten, titanium, cobalt, manganese, iron, nickel, or a transition metal; (d) boron nitride, or (e) a combination thereof.

In another preferred rechargeable lithium cell (e.g. a lithium metal secondary cell or a lithium-ion cell), the cathode active material contains an organic material or polymeric material selected from Poly(anthraquinonyl sulfide) (PAQS), lithium oxocarbons (including squarate, croconate, and rhodizonate lithium salts), oxacarbon (including quinines, acid anhydride, and nitrocompound), 3,4,9,10-perylenetetracarboxylic dianhydride (PTCDA), poly(anthraquinonyl sulfide), pyrene-4,5,9,10-tetraone (PYT), polymer-bound PYT, Quino(triazene), redox-active organic material (redox-active structures based on multiple adjacent carbonyl groups (e.g., "$C_6O_6$"-type structure, oxocarbons), Tetracyanoquinodimethane (TCNQ), tetracyanoethylene (TCNE), 2,3,6,7,10,11-hexamethoxytriphenylene (HMTP), poly(5-amino-1,4-dyhydroxy anthraquinone) (PADAQ), phosphazene disulfide polymer ([(NPS$_2$)$_3$]n), lithiated 1,4,5,8-naphthalenetetraol formaldehyde polymer, Hexaazatrinaphtylene (HATN), Hexaazatriphenylene hexacarbonitrile (HAT(CN) 6), 5-Benzylidene hydantoin, Isatine lithium salt, Pyromellitic diimide lithium salt, tetrahydroxy-p-benzoquinone derivatives (THQLi$_4$), N,N'-diphenyl-2,3,5,6-tetraketopiperazine (PHP), N,N'-diallyl-2,3,5,6-tetraketopiperazine (AP), N,N'-dipropyl-2,3,5,6-tetraketopiperazine (PRP), a thioether polymer, a quinone compound, 1,4-benzoquinone, 5,7,12,14-pentacenetetrone (PT), 5-amino-2,3-dihydro-1,4-dyhydroxy anthraquinone (ADDAQ), 5-amino-1,4-dyhydroxy anthraquinone (ADAQ), calixquinone, $Li_4C_6O_6$, $Li_2C_6O_6$, $Li_6C_6O_6$, or a combination thereof.

The thioether polymer may be selected from Poly[methanetetryl-tetra(thiomethylene)] (PMTTM), Poly(2,4-dithiopentanylene) (PDTP), or Poly(ethene-1,1,2,2-tetrathiol) (PETT) as a main-chain thioether polymer, in which sulfur atoms link carbon atoms to form a polymeric backbones. The side-chain thioether polymers have polymeric main-chains that consist of conjugating aromatic moieties, but having thioether side chains as pendants. Among them Poly(2-phenyl-1,3-dithiolane) (PPDT), Poly(1,4-di(1,3-dithiolan-2-yl)benzene) (PDDTB), poly(tetrahydrobenzodithiophene) (PTHBDT), and poly[1,2,4,5-tetrakis(propylthio)benzene] (PTKPTB) have a polyphenylene main chain, linking thiolane on benzene moieties as pendants. Similarly, poly[3,4(ethylenedithio)thiophene] (PEDTT) has polythiophene backbone, linking cyclo-thiolane on the 3,4-position of the thiophene ring.

In yet another preferred rechargeable lithium cell, the cathode active material contains a phthalocyanine compound selected from copper phthalocyanine, zinc phthalocyanine, tin phthalocyanine, iron phthalocyanine, lead phthalocyanine, nickel phthalocyanine, vanadyl phthalocyanine, fluorochromium phthalocyanine, magnesium phthalocyanine, manganous phthalocyanine, dilithium phthalocyanine, aluminum phthalocyanine chloride, cadmium phthalocyanine, chlorogallium phthalocyanine, cobalt phthalocyanine, silver phthalocyanine, a metal-free phthalocyanine, a chemical derivative thereof, or a combination thereof. This class of lithium secondary batteries has a high capacity and high energy density.

Still another preferred embodiment of the present invention is a rechargeable lithium-sulfur cell or lithium-ion sulfur cell containing a sulfur cathode having sulfur or lithium polysulfide as a cathode active material.

In any of the aforementioned rechargeable lithium cell (e.g. a lithium metal secondary cell or a lithium-ion cell), the liquefied gas solvent may be mixed with an organic co-solvent selected from 1,3-dioxolane (DOL), 1,2-dimethoxyethane (DME), tetraethylene glycol dimethylether (TEGDME), poly(ethylene glycol) dimethyl ether (PEGDME), diethylene glycol dibutyl ether (DEGDBE), 2-ethoxyethyl ether (EEE), sulfone, sulfolane, ethylene carbonate (EC), dimethyl carbonate (DMC), methylethyl carbonate (MEC), diethyl carbonate (DEC), ethyl propionate, methyl propionate, propylene carbonate (PC), gamma.-butyrolactone (γ-BL), acetonitrile (AN), ethyl acetate (EA), propyl formate (PF), methyl formate (MF), toluene, xylene, methyl acetate (MA), fluoroethylene carbonate (FEC), vinylene carbonate (VC), allyl ethyl carbonate (AEC), a hydrofloroether, a room temperature ionic liquid solvent, or a combination thereof.

The electrolyte may further contain a liquid co-solvent mixed with a liquefied gas solvent wherein the liquid co-solvent is selected from the group consisting of hydrofluoro ether (HFE), trifluoro propylene carbonate (FPC), methyl nonafluorobutyl ether (MFE), fluoroethylene carbonate (FEC), tris(trimethylsilyl)phosphite (TTSPi), triallyl phosphate (TAP), ethylene sulfate (DTD), 1,3-propane sultone (PS), propene sultone (PES), diethyl carbonate (DEC), alkylsiloxane (Si—O), alkyylsilane (Si—C), liquid oligomeric silaxane (—Si—O—Si—), ttetraethylene glycol dimethylether (TEGDME), and combinations thereof.

In an embodiment, the electrolyte further contains an ionic liquid solvent and a first organic liquid solvent-to-ionic liquid solvent ratio is greater than 1/1, preferably greater than 3/1. The ionic liquid solvent is preferably selected from a room temperature ionic liquid having a cation selected from tetraalkylammonium, di-, tri-, or tetra-alkylimidazolium, alkylpyridinium, dialkyl-pyrrolidinium, dialkylpiperidinium, tetraalkylphosphonium, trialkylsulfonium, or a combination thereof. The room temperature ionic liquid preferably has an anion selected from $BF_4^-$, $B(CN)_4^-$, $CH_3BF_3^-$, $CH_2CHBF_3^-$, $CF_3BF_3^-$, $C_2F_5BF_3^-$, n-$C_3F_7BF_3^-$, n-$C_4F_9BF_3^-$, $PF_6^-$, $CF_3CO_2^-$, $CF_3SO_3^-$, $N(SO_2CF_3)_2^-$, $N(COCF_3)(SO_2CF_3)^-$, $N(SO_2F)_2^-$, $N(CN)_2^-$, $C(CN)_3^-$, $SCN^-$, $SeCN^-$, $CuCl_2^-$, $AlCl_4^-$, $F(HF)_{23}^-$, or a combination thereof.

In any of the aforementioned rechargeable lithium cell, the anode may contain an anode active material selected from lithium metal, a lithium metal alloy, a mixture of lithium metal or lithium alloy with a lithium intercalation compound, a lithiated compound, lithiated titanium dioxide, lithium titanate, lithium manganate, a lithium transition metal oxide, $Li_4Ti_5O_{12}$, or a combination thereof.

Alternatively, the anode may contain an anode active material selected from the group consisting of: (a) silicon (Si), germanium (Ge), tin (Sn), lead (Pb), antimony (Sb), bismuth (Bi), zinc (Zn), aluminum (Al), nickel (Ni), cobalt (Co), manganese (Mn), titanium (Ti), iron (Fe), and cadmium (Cd), and lithiated versions thereof; (b) alloys or intermetallic compounds of Si, Ge, Sn, Pb, Sb, Bi, Zn, Al, or Cd with other elements, and lithiated versions thereof, wherein said alloys or compounds are stoichiometric or non-stoichiometric; (c) oxides, carbides, nitrides, sulfides, phosphides, selenides, and tellurides of Si, Ge, Sn, Pb, Sb, Bi, Zn, Al, Fe, Ni, Co, Ti, Mn, or Cd, and their mixtures or composites, and lithiated versions thereof; (d) salts and hydroxides of Sn and lithiated versions thereof; (e) carbon or graphite materials and prelithiated versions thereof and combinations thereof. The carbon or graphite materials may be selected from the group consisting of natural graphite particles, synthetic graphite particles, needle cokes, electrospun nanofibers, vapor-grown carbon or graphite nanofibers, carbon or graphite whiskers, carbon nano-tubes, carbon nanowires, sheets and platelets of pristine graphene, graphene oxide, reduced graphene oxide, doped graphene or graphene oxide, and chemically functionalized graphene, and combinations thereof.

Another preferred rechargeable lithium cell is a lithium-air cell having a higher round-trip efficiency or higher resistance to capacity decay as compared to a corresponding lithium-air cell that has an electrolyte salt concentration x (molecular ratio) lower than 0.2.

The rechargeable lithium cell may further comprise a layer of protective material disposed between the anode and the electrolyte wherein the protective material is a lithium ion conductor.

The rechargeable lithium cell may further comprise a cathode current collector selected from aluminum foil, carbon- or graphene-coated aluminum foil, stainless steel foil or web, carbon- or graphene-coated steel foil or web, carbon or graphite paper, carbon or graphite fiber fabric, flexible graphite foil, graphene paper or film, or a combination thereof. A web means a screen-like structure or a metal foam, preferably having interconnected pores or through-thickness apertures. The lithium cell may further comprise an anode current collector selected from copper foil or web, carbon- or graphene-coated copper foil or web, stainless steel foil or web, carbon- or graphene-coated steel foil or web, titanium foil or web, carbon- or graphene-coated titanium foil or web carbon or graphite paper, carbon or graphite fiber fabric, flexible graphite foil, graphene paper or film, or a combination thereof.

The presently invented lithium-sulfur cell provides a reversible specific capacity of typically no less than 800 mAh per gram based on the total weight of exfoliated graphite worms and sulfur (or sulfur compound or lithium polysulfide) combined. More typically and preferably, the reversible specific capacity is no less than 1,000 mAh per gram and often exceeds 1,200 mAh per gram. The high specific capacity of the presently invented cathode, when in combination with a lithium anode, leads to a cell specific energy of no less than 600 Wh/Kg based on the total cell weight including anode, cathode, electrolyte, separator, and current collector weights combined. In many cases, the cell specific energy is higher than 800 Wh/Kg and, in some examples, exceeds 1,000 Wh/kg.

The rechargeable lithium cell of the present invention featuring a non-flammable quasi-solid electrolyte is not limited to lithium metal-sulfur cell or lithium-ion cell. This safe and high-performing electrolyte can be used in any lithium metal secondary cell (lithium metal-based anode coupled with any cathode active material) and any lithium-ion cell.

These and other advantages and features of the present invention will become more transparent with the description of the following best mode practice and illustrative examples.

DETAILED DESCRIPTION OF PREFERRED EMBODIMENTS

Figure 1:
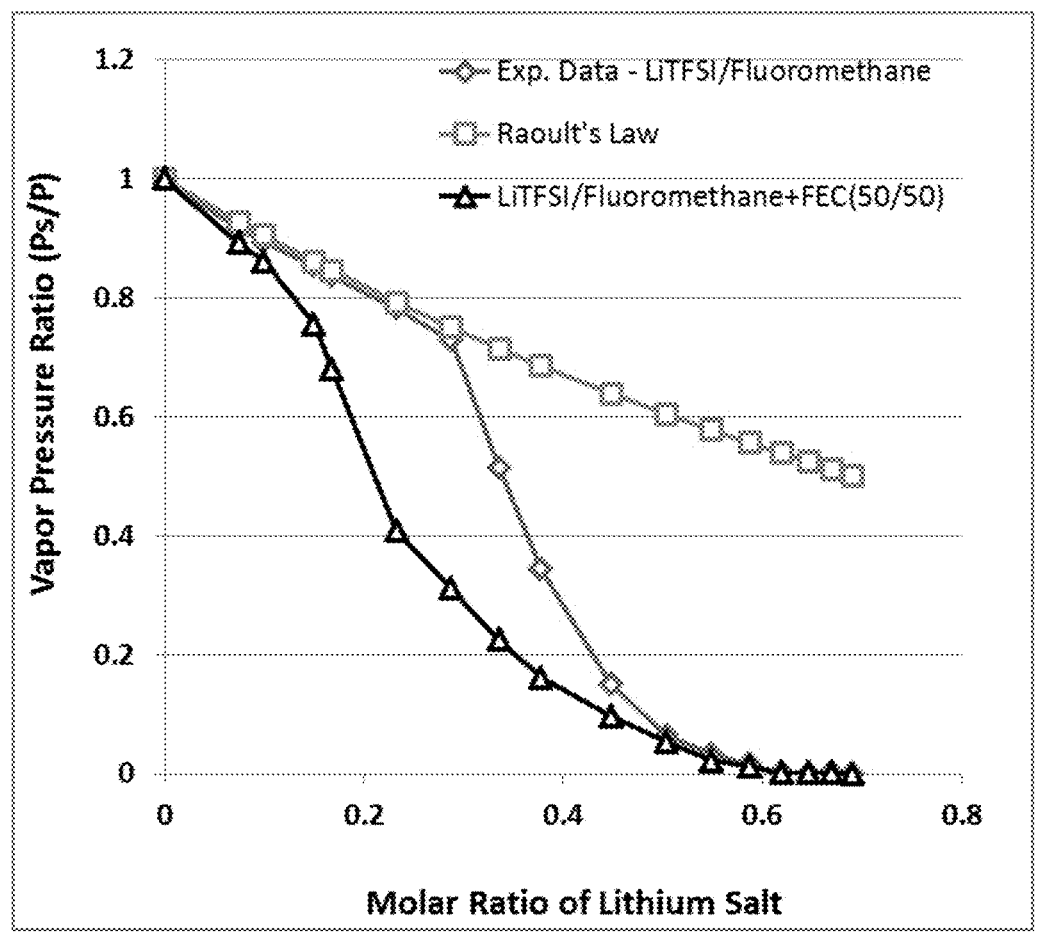
FIG. 1 Vapor pressure ratio data ($p_s/p$=vapor pressure of solution/vapor pressure of solvent alone) as a function of the lithium salt molecular ratio x, LiTFSI/(LiTFSI+Fluoromethane) or LiTFSI/(LiTFSI+Fluoromethane-FEC-50/50), along with the theoretical predictions based on the classic Raoult's Law.
Figure 2:
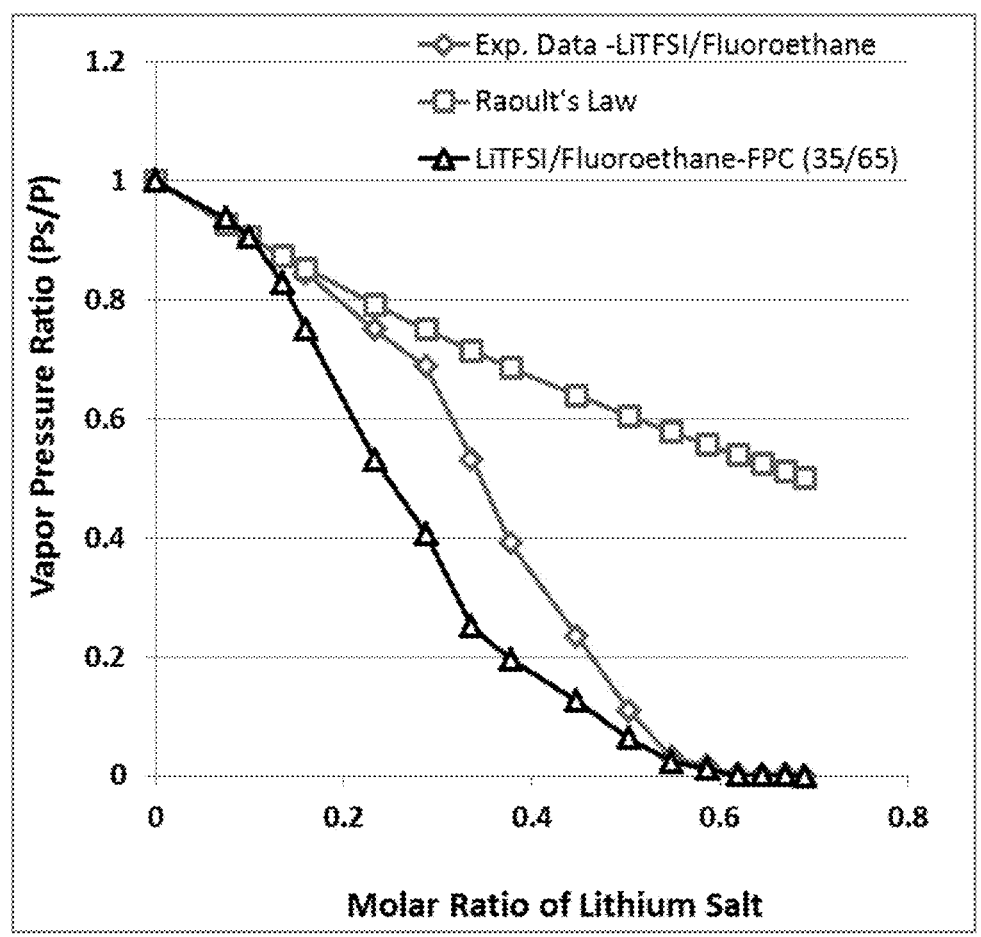
FIG. 2 Vapor pressure ratio data ($p_s/p$=vapor pressure of solution/vapor pressure of solvent alone) as a function of the lithium salt molecular ratio x, LiTFSI/(LiTFSI+Fluoroethane) or LiTFSI/(LiTFSI+Fluoroethane-FPC-35/65), along with the theoretical predictions based on classic Raoult's Law.
Figure 3:
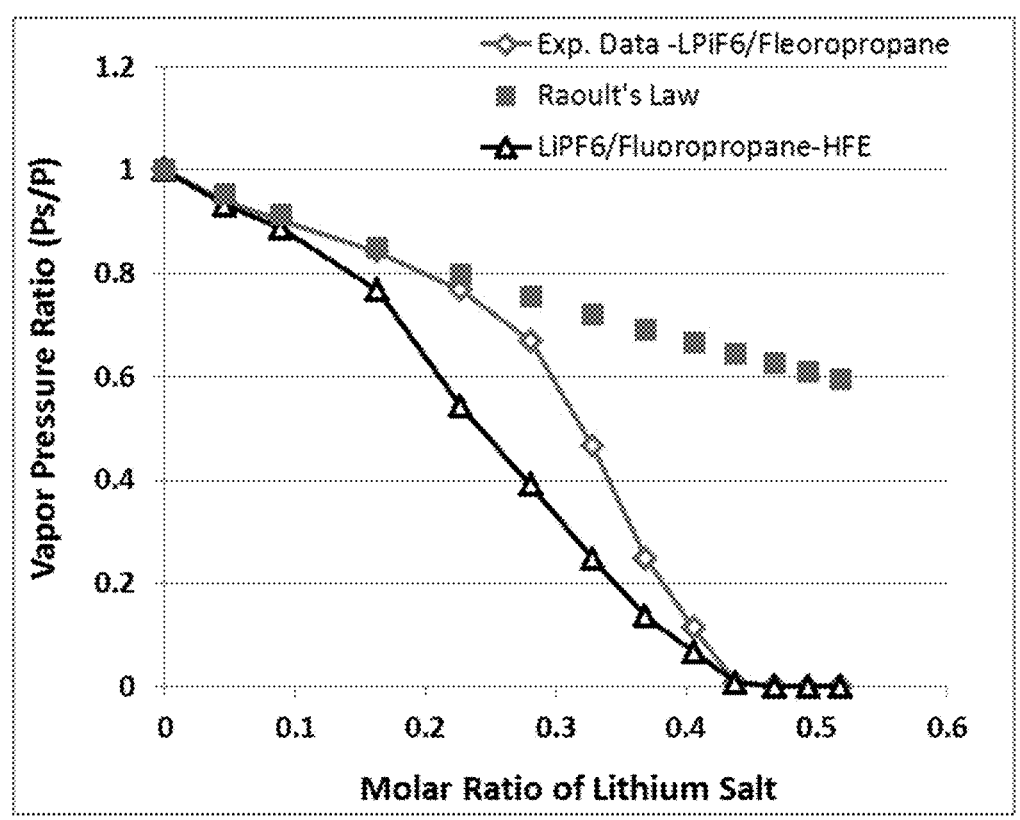
FIG. 3 Vapor pressure ratio data ($p_s/p$=vapor pressure of solution/vapor pressure of solvent alone) as a function of the lithium salt molecular ratio x, $LiPF_6$/($LiPF_6$+Fluoropropane) or $LiPF_6$/($LiPF_6$+Fluoropropane-HFE-15/85), along with the theoretical predictions based on classic Raoult's Law.
Figure 4:
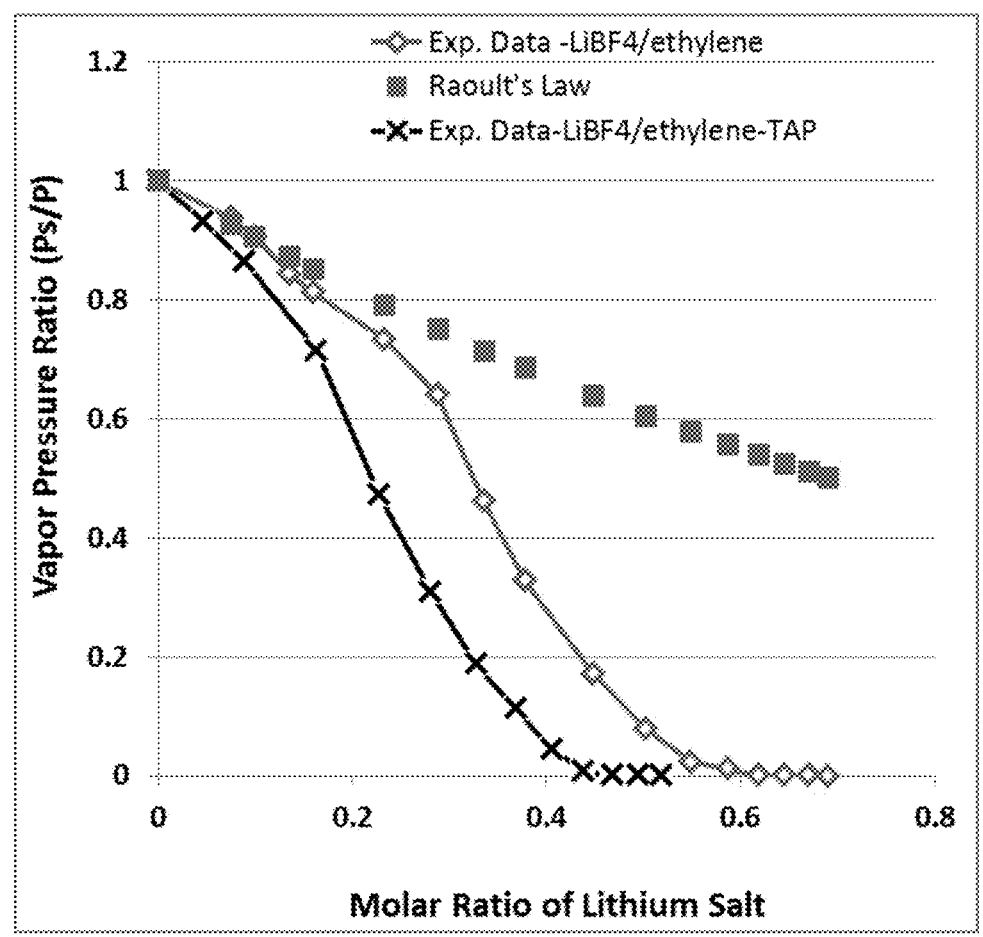
FIG. 4 Vapor pressure ratio data ($p_s/p$=vapor pressure of solution/vapor pressure of solvent alone) as a function of the lithium salt molecular ratio x, $LiBF_4$/($LiBF_4$+ethylene) and $LiBF_4$/($LiBF_4$+ethylene-TAP-80/20), along with the theoretical predictions based on classic Raoult's Law.

The present invention provides a safe and high-performing rechargeable lithium battery, which can be any of various types of lithium-ion cells or lithium metal cells. A high degree of safety is imparted to this battery by a novel and unique electrolyte that is essentially non-flammable and would not initiate a fire or sustain a fire and, hence, would not pose explosion danger. This invention has solved the very most critical issue that has plagued the lithium-metal and lithium-ion industries for more than two decades.

As indicated earlier in the Background section, a strong need exists for a safe, non-flammable, yet easily processable electrolyte system for a rechargeable lithium cell. A highly innovative and surprising feature of the present invention is making the usually flammable and combustible liquefied gases non-flammable, as well as a suitable battery electrolyte solvent. The lithium salt-retained liquefied gases also become capable of delivering high lithium ion transport rates.

Thus, the present invention provides a non-flammable electrolyte for a lithium battery. The electrolyte contains lithium salt-retained liquefied gas having a lithium salt dissolved in or mixed with a liquefied gas solvent having a lithium salt concentration greater than 1.0 M so that said electrolyte exhibits a vapor pressure less than 1 kPa when measured at 20° C., a vapor pressure less than 60% of the vapor pressure of the liquefied gas solvent alone, a flash point at least 20 degrees Celsius higher than a flash point of the liquefied gas solvent alone, a flash point higher than 150° C., or no flash point, wherein the liquefied gas solvent is selected from methane, fluoromethane, difluoromethane, chloromethane, dichloromethane, ethane, fluoroethane, difluoroethane, tetrafluoroethane, chloroethane, dichloroethane, tetrachloroethane, propane, fluoropropane, chloropropane, ethylene, fluoroethylene, chloroethylene, or a combination thereof.

The inventive cell comprises a cathode having a cathode active material and/or a conductive cathode-supporting structure, an anode having an anode active material and/or a conductive supporting nano-structure, an optional separator electronically separating the anode and the cathode, a liquefied gas-based electrolyte in contact with the cathode active material (or the cathode conductive supporting structure for a Li-air cell) and the anode active material, wherein the electrolyte contains a lithium salt dissolved in or mixed with a liquefied gas solvent with a lithium salt molecular ratio sufficiently high so that the electrolyte exhibits a vapor pressure less than 1.0 kPa (preferably <0.1 kPa and further preferably <0.01 kPa) or less than 0.6 (60%) of the vapor pressure of the liquefied gas solvent alone (when measured at 20° C.), a flash point at least 20 degrees Celsius higher than a flash point of the liquefied gas solvent alone (when no lithium salt is present), a flash point higher than 150° C., or no detectable flash point at all. The liquefied gas solvent is preferably selected from methane, fluoromethane, difluoromethane, chloromethane, dichloromethane, ethane, fluoroethane, difluoroethane, tetrafluoroethane, chloroethane, dichloroethane, tetrachloroethane, propane, fluoropropane, chloropropane, ethylene, fluoroethylene, chloroethylene, or a combination thereof.

Most surprising and of tremendous scientific and technological significance is our discovery that the flammability of a liquefied gas solvent can be effectively suppressed provided that a sufficiently high amount of a lithium salt is added to and dissolved in this "solvent" to form a near solid-like or quasi-solid electrolyte. In general, such a quasi-solid electrolyte exhibits a vapor pressure less than 1 kPa (typically <0.01 kPa) and often less than 0.001 kPa (when measured at 20° C.) and less than 0.1 kPa and often less than 0.01 kPa (when measured at 100° C.). (The vapor pressures of the corresponding neat liquefied gas solvent, without any lithium salt dissolved therein, are typically significantly higher.) In many cases, with a lithium salt concentration >1.5 M (particularly >2.5 M), the vaporized gas molecules from a liquefied gas in the above list are practically too few to be detected.

A highly significant observation is that the high concentration of the lithium salt dissolved in an otherwise highly volatile solvent (a large molecular ratio or molar fraction of lithium salt, typically >0.2, more typically >0.3, and often >0.4 or even >0.5) can dramatically curtail the amount of volatile solvent molecules that can escape into the vapor phase in a thermodynamic equilibrium condition. In many cases, this has effectively prevented the flammable liquefied gas molecules from initiating a flame even at an extremely high temperature (e.g. using a torch). The flash point of the quasi-solid electrolyte is typically at least 20 degrees (often >50 degrees) higher than the flash point of the liquefied gas solvent alone. In most of the cases, either the flash point is higher than 150° C. or no flash point can be detected. The electrolyte just would not catch on fire. Furthermore, any accidentally initiated flame does not sustain for longer than 3 seconds. This is a highly significant discovery, considering the notion that fire and explosion concern has been a major impediment to widespread acceptance of battery-powered electric vehicles. Furthermore, liquefied gases are meant to be flammable and combustible (as a fuel) and this flammability can be effectively suppressed by using the approach of retaining gas molecules with a lithium salt. This new technology could significantly and positively impact the emergence of a vibrant EV industry.

However, an excessively high salt concentration could possibly result in an excessively high electrolyte viscosity. When the lithium salt concentration exceeds approximately 3.5 M (molecular ratio or fraction >0.28), it becomes very difficult to inject the electrolyte into a well-packed dry cell to finish the cell production procedure. The injection becomes totally impossible when the salt concentration exceeds 5.0 M (molecular fraction >0.4). This has prompted us to search for solutions to this problem of having two mutually exclusive requirements (high salt concentration for non-flammability and low salt concentration for electrolyte fluidity). After extensive and in-depth studies, we have come to discover that these conflicting issues can be resolved provided certain volatile liquid additives (or co-solvents) are added to the liquefied gas solvent to form a mixture in which the lithium salt is dissolved to form the electrolyte. There can be one liquefied gas solvent with one liquid additive, one liquefied gas solvent with two liquid additives, two liquefied gas solvents with one liquid additive, etc. in the liquid mixture. There can be multiple liquefied solvents mixed with multiple liquid additives (co-solvents). The volatile co-solvent is later partially or totally removed prior to sealing the battery. Quite unexpectedly, the removal of this co-solvent typically did not lead to precipitation or crystallization of the lithium salt out of the solution even though the solution would have been in a highly supersaturated state. This novel and unique approach appears to have produced a material state wherein most of the solvent molecules are retained or captured by lithium salt ions that are not volatile. Hence, very few solvent molecules are able to escape into the vapor phase. Consequently, very few volatile gas molecules can be present to initiate or sustain a flame. This has not been suggested as technically possible or viable in any previous report.

Alternatively, one may dissolve a lithium salt in a liquefied gas under a high pressure environment (at least equal to the saturation vapor pressure, but typically 1 to 10 atm at 20° C.) to a maximum salt concentration $C_1$ and then remove (vaporize) the gas at a higher temperature and/or a lower pressure (and preferably under a pumping operation to pump out a desired amount of the previously liquefied gas) to achieve a significantly higher salt concentration $C_2$ ($C_2 > C_1$). This treatment also puts the lithium salt in a supersaturated state without crystallization.

From the perspective of fundamental chemistry principles, addition of solute molecules to a liquid elevates the boiling temperature of the liquid and reduces its vapor pressure and freezing temperature. These phenomena, as well as osmosis, depend only on the solute concentration and not on its type, and are called colligative properties of solutions. The original Raoult's law provides the relationship between the ratio of the vapor pressure ($p_s$) of a solution to the vapor pressure (p) of the pure liquid and the molar fraction (molecular ratio) of the solute (x):

$$p_s/p = e^{-x} \quad \text{Eq. (1a)}$$

For a dilute solution, $x \ll 1$ and, hence, $e^{-x} \approx 1-x$. Thus, for the special cases of low solute molar fractions, one obtains a more familiar form of Raoult's law:

$$p_s/p = 1-x \quad \text{Eq. (1b)}$$

In order to determine if the classic Raoult's law can be used to predict the vapor pressures of highly concentrated electrolytes, we proceeded to investigate a broad array of lithium salt/organic solvent combinations. Some of the examples of our research results are summarized in FIG. 1 to FIG. 4, where the experimental pip values are plotted as a function of the molecular ratio (molar fraction, x) for several salt/solvent combinations. Also plotted for comparison purpose is a curve based on the classic Raoult's law, Eq. (1a). It is clear that, for all types of electrolytes, the pip values follow the Raoult's law prediction until the molar fraction x reaches approximately 0.2 (without electrolyte additive), beyond which the vapor pressure rapidly drops to essentially zero (barely detectable). When a vapor pressure is lower than a threshold, no flame would be initiated, and the presence of a certain type of additive can help to shift the threshold to a lower molecular fraction value (lower salt concentration value). The useful additives include from Hydrofluoro ether (HFE), Trifluoro propylene carbonate (FPC), Methyl nonafluorobutyl ether (MFE), Fluoroethylene carbonate (FEC), Tris(trimethylsilyl)phosphite (TTSPi), Triallyl phosphate (TAP), Ethylene sulfate (DTD), 1,3-propane sultone (PS), Propene sultone (PES), Diethyl carbonate (DEC), Alkylsiloxane (Si—O), Alkyylsilane (Si—C), liquid oligomeric silaxane (—Si—O—Si—), Ttetraethylene glycol dimethylether (TEGDME), or a combination thereof. The present invention provides a platform materials chemistry approach to effectively suppress the initiation of flame and still ensure that the electrolyte remains conducive to injection into dry battery cells.

Although deviations from Raoult's law are not uncommon in science, this type of curve for the $p_s/p$ values has never been observed for any binary solution systems. In particular, there has been no study reported on the vapor pressure of high concentration battery electrolytes (with a high molecular fraction, e.g. >0.15) for safety considerations. This is truly unexpected and of technological and scientific significance.

Another surprising element of the present invention is the notion that we are able to dissolve a high concentration of a lithium salt in the liquefied gas solvent to form a quasi-solid electrolyte (having a lithium ion transport rate) suitable for use in a rechargeable lithium battery. Expressed in a more easily recognizable term, this concentration is typically greater than 1.5 M (mole/liter), and can be greater than 2M, 5M, 7M, or even 10M (although it is undesirable to go beyond 7 M in the instant invention). Such a high concentration of lithium salt in a solvent has not been generally considered possible. However, one must understand that the vapor pressure of a solution cannot be predicted directly and straightforwardly from the concentration value in terms of M (mole/liter). Instead, for a lithium salt, the molecular ratio x in Raoult's law is the sum of the molar fractions of positive ions and negative ions, which is proportional to the degree of dissociation of a lithium salt in a particular solvent at a given temperature. The mole/liter concentrations do not provide the best information for prediction of vapor pressures.

In general, it has not been possible to achieve such a high concentration of lithium salt (e.g., x=0.2-0.7) in an organic solvent or liquefied solvent used in a battery electrolyte. After an extensive and in-depth study, we came to further discover that the apparent solubility of a lithium salt in a particular liquefied gas solvent could be significantly increased if (a) a highly volatile co-solvent is added to increase the amount of lithium salt dissolved in the solvent mixture first and then (b) this volatile co-solvent is partially or totally removed once the dissolution procedure is completed. Quite unexpectedly, the removal of this co-solvent typically did not lead to precipitation or crystallization of the lithium salt out of the solution even though the solution would have been in a highly supersaturated state. This novel and unique approach appears to have produced a material state wherein most of the solvent molecules are captured or held in place by lithium salt ions that are not volatile (actually the lithium salt being like a solid). Therefore, very few volatile solvent molecules are able to escape into the vapor phase and, hence, very few "flammable" gas molecules are present to help initiate or sustain a flame. The additives in the above list appear to be capable of further reducing the amount of escaped gas molecules and, hence, helping to reduce or eliminate flammability. This has not been suggested as technically possible or viable in the prior art.

Furthermore, a skilled artisan in the field of chemistry or materials science would have anticipated that such a high salt concentration should make the electrolyte behave like a solid with an extremely high viscosity and, hence, this electrolyte should not be amenable to fast diffusion of lithium ions therein. Consequently, the artisan would have expected that a lithium battery containing such a solid-like electrolyte (1.5 M to 14 M) would not and could not exhibit a high capacity at a high charge-discharge rate or under a high current density condition (i.e. the battery should have a poor rate capability). Contrary to these expectations by a person of ordinary skills or even exceptional skills in the art, all the lithium cells containing such a quasi-solid electrolyte deliver high energy density and high power density for a long cycle life. It appears that the quasi-solid electrolytes (containing molecules of commonly used liquefied gases and their derivatives) as herein invented and disclosed are conducive to facile lithium ion transport. This surprising observation is related to a high lithium ion transference number (TN), to be further explained in a later section of this specification. We have found that the quasi-solid electrolytes provides a TN greater than 0.4 (typically in the range of 0.4-0.8), in contrast to the typical values of 0.1-0.2 in all lower concentration electrolytes (e.g. <1.5 M) used in all current Li-ion and Li—S cells.

Figure 5:
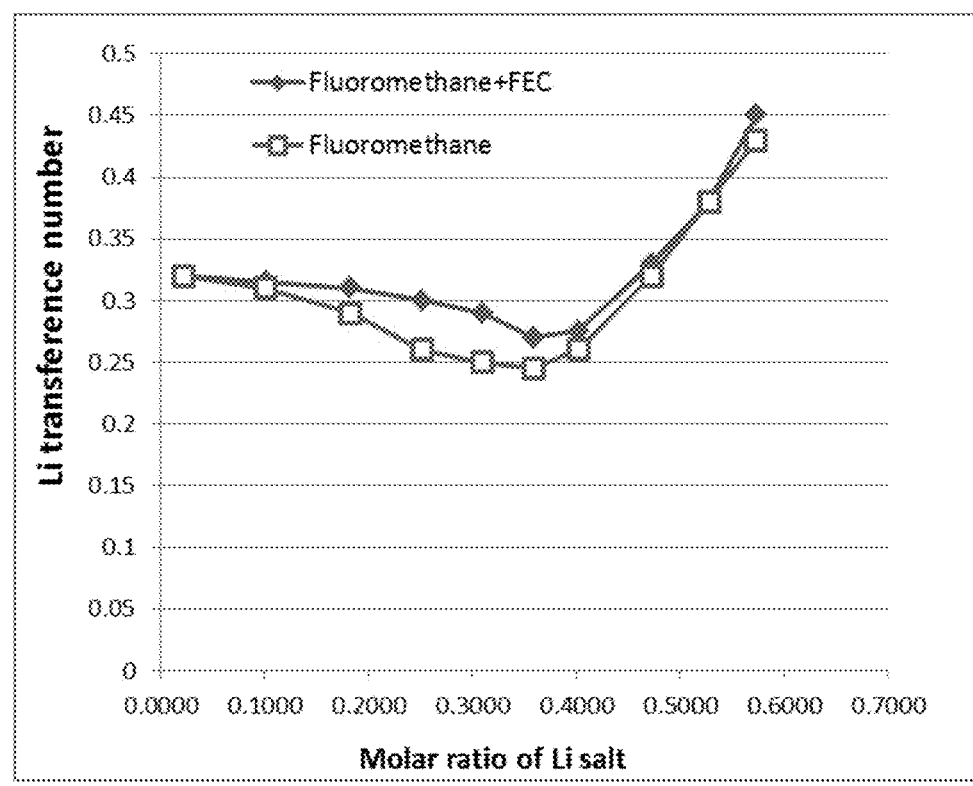
FIG. 5 The $Li^-$ ion transference numbers of electrolytes (e.g. LiTFSI salt/(Fluoromethane) solvents) in relation to the lithium salt molecular ratio x, with or without the electrolyte co-solvent FEC.
Figure 6:
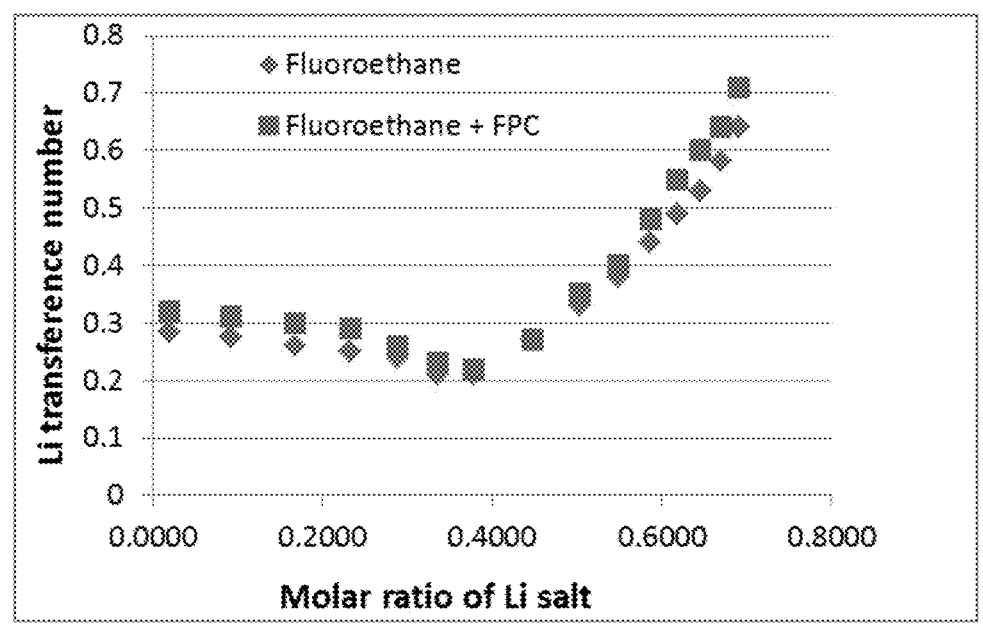
FIG. 6 The $Li^-$ ion transference numbers of electrolytes (e.g. LiTFSI salt/(Fluoroethane) solvents) in relation to the lithium salt molecular ratio x, with or without the electrolyte co-solvent FPC.
Figure 7:
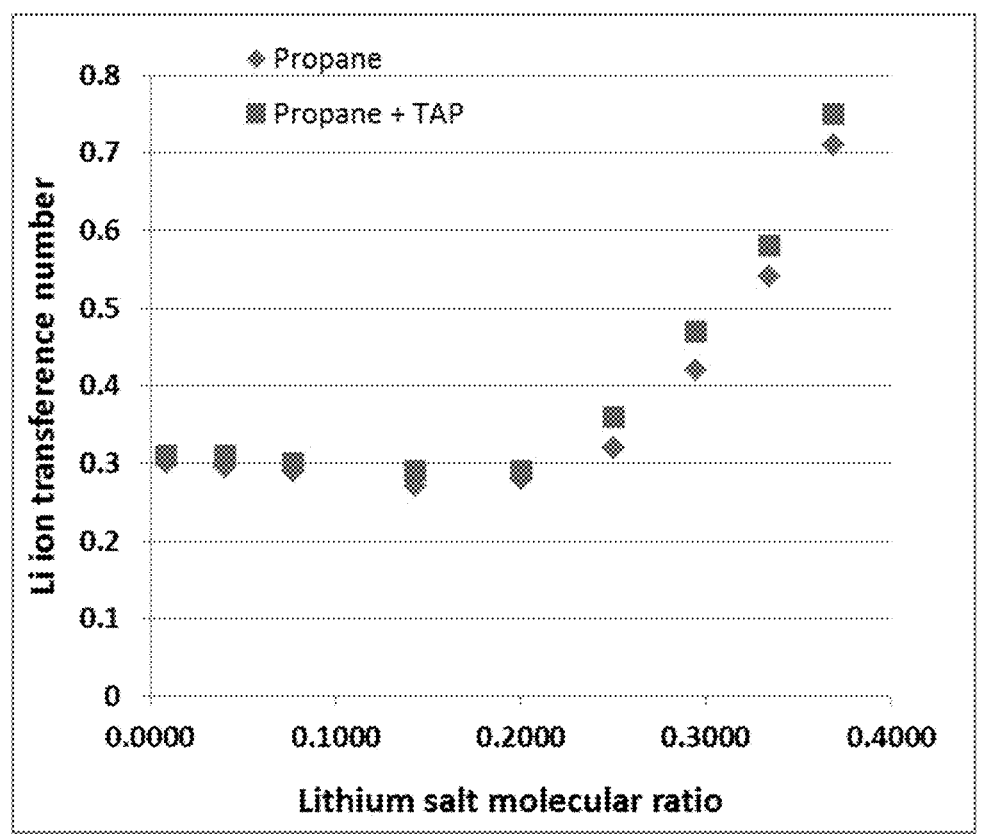
FIG. 7 The $Li^-$ ion transference numbers of electrolytes (e.g. LiTFSI salt/(propane) solvents) in relation to the lithium salt molecular ratio x, with or without the electrolyte co-solvent TAP.

As indicated in FIG. 5 to FIG. 7, the $Li^+$ ion transference number in low salt concentration electrolytes decreases with increasing concentration from x=0 to x=0.2-0.3. However, beyond molecular ratios of x=0.2-0.3, the transference number increases with increasing salt concentration, indicating a fundamental change in the $Li^+$ ion transport mechanism. Not wishing to be bound by theory, but we would like to offer the following scientifically plausible explanations: When $Li^+$ ions travel in a low salt concentration electrolyte (e.g. x<0.2), each $Li^+$ ion drags one or more solvating anions along with it. The coordinated migration of such a cluster of charged species can be further impeded if the fluid viscosity is increased (i.e. if more salt is added to the solvent).

Fortunately, when an ultra-high concentration of lithium salt (e.g., with x>0.2) is present, $Li^+$ ions could significantly out-number the available solvating anions or solvent molecules that otherwise could cluster the lithium ions, forming multi-ion complex species and slowing down the diffusion process of $Li^+$ ions. This high $Li^+$ ion concentration makes it possible to have more "free Li+ ions" (those acting alone without being clustered), thereby providing a high Li+ transference number (hence, a facile Li+ transport). In other words, the lithium ion transport mechanism changes from a multi-ion complex-dominating one (with a larger hydrodynamic radius) to single ion-dominating one (with a smaller hydrodynamic radius) having a large number of available free Li+ ions. This observation has further asserted that Li+ ions can operate on liquefied gas-based quasi-solid electrolytes without compromising the rate capability of a Li—S cell. Yet, these highly concentrated electrolytes are non-flammable and safe. These combined features and advantages for battery applications have never been taught or even slightly hinted in any previous report. Theoretical aspects of ion transference number of quasi-solid electrolytes are now presented below:

In selecting an electrolyte system for a battery, the ionic conductivity of lithium ions is an important factor to consider. The ionic conductivity of Li+ ions in an organic liquid-based electrolyte is on the order of $10^{-3}$-$10^{-2}$ S/cm and that in a solid state electrolyte is typically in the range of $10^{-4}$-$10^{-6}$ S/cm. Due to the low ionic conductivity, solid-state electrolytes have not been used to any significant extent in any battery system. This is a pity since solid-state electrolyte is resistant to dendrite penetration in a lithium metal secondary cell and does not allow for undesirable dissolution of lithium polysulfide in a Li—S cell. The charge-discharge capacities of Li—S cells with a solid electrolyte are extremely low, typically 1 order of magnitude lower than the theoretical capacity of sulfur. In contrast, the ionic conductivity of our quasi-solid electrolytes is typically in the range of $10^{-4}$-$8 \times 10^{-3}$ S/cm, sufficient for use in a rechargeable battery.

However, the overall ionic conductivity is not the only important transport parameter of a battery electrolyte. The individual transference numbers of cations and anions are also important. For instance, when viscous liquids are used as electrolytes in lithium batteries high transference numbers of Li+ ions in the electrolyte are needed.

The ion transport and diffusion in a liquid electrolyte consisting of only one type of cation (i.e. Li+) and one type of anion, plus a liquid solvent or a mixture of two liquid solvents, may be studied by means of AC impedance spectroscopy and pulsed field gradient NMR techniques. The AC impedance provides information about the overall ionic conductivity, and NMR allows for the determination of the individual self-diffusion coefficients of cations and anions. Generally, the self-diffusion coefficients of the cations are slightly higher than those of the anions. The Haven ratio calculated from the diffusion coefficients and the overall ionic conductivity is typically in the range from 1.3 to 2, indicating that transport of ion pairs or ion complexes (e.g. clusters of Li+-solvating molecules) is an important feature in electrolytes containing a low salt concentration.

The situation becomes more complicated when either two different lithium salts or one ionic liquid (as a lithium salt or liquid solvent) is added to the electrolyte, resulting in a solution having at least 3 or 4 types of ions. In this case, as an example, it is advantageous to use a lithium salt containing the same anion as in the solvating ionic liquid, since the amount of dissolvable lithium salt is higher than in a mixture with dissimilar anions. Thus, the next logical question to ask is whether it is possible to improve the Li+ transference number by dissolving more lithium salt in liquid solvent.

The relation between the overall ionic conductivity of a three-ion liquid mixture, $\sigma_{dc}$, and the individual diffusion coefficients of the ions, Di, may be given by the Nernst-Einstein equation:

$$\sigma_{dc} = (e^2/k_B T H_R)[(N_{Li^+})(D_{Li^+}) + (N_{A^+})(N_{A^+}) + (N_B^-)(D_B^-)] \qquad \text{Eq. (2)}$$

Here, e and $k_B$ denote the elementary charge and Boltzmann's constant, respectively, while $N_i$ are the number densities of individual ions. The Haven ratio, $H_R$, accounts for cross correlations between the movements of different types of ions.

Simple ionic liquids with only one type of cation and anion are characterized by Haven ratios being typically in the range from 1.3 to 2.0. A Haven ratio larger than unity indicates that ions of dissimilar charges move preferentially into the same direction (i.e. ions transport in pairs or clusters). Evidence for such ion pairs can be found using Raman spectra of various electrolytes. The values for the Haven ratios in the three-ion mixtures are in the range from 1.6 to 2.0. The slightly higher $H_R$ values as compared to the electrolytes with x=0 indicate that pair formation is more prominent in the mixtures.

For the same mixtures, the overall ionic conductivity of the mixtures decreases with increasing lithium salt content x. This conductivity drop is directly related to a drop of the individual self-diffusion coefficients of all ions. Furthermore, studies on different mixtures of ionic liquids with lithium salts have shown that the viscosity increases with increasing lithium salt content x. These findings suggest that the addition of lithium salt leads to stronger ionic bonds in the liquid mixture, which slow down the liquid dynamics. This is possibly due to the Coulomb interaction between the small lithium ions and the anions being stronger than the Coulomb interactions between the larger organic cations and the anions. Thus, the decrease of the ionic conductivity with increasing lithium salt content x is not due to a decreasing number density of mobile ions, but to a decreasing mobility of the ions.

In order to analyze the individual contributions of the cations and anions to the overall ionic conductivity of the mixtures, one may define the apparent transference numbers $t_i$ by:

$$t_i = N_i Di/(\Sigma N_i Di) \qquad \text{Eq. (3)}$$

As an example, in a mixture of N-butyl-N-methyl-pyrrolidinium bis(trifluoromethanesulfonyl) imide (BMP-TFSI) and lithium bis(trifluoromethanesulfonyl)imide (Li-TFSI), containing Li+, BMP+, and TFSI− ions, the apparent lithium transference number $t_{Li}$ increases with increasing Li-TFSI content; at x=0.377, $t_{Li}$=0.132 (vs. $t_{Li}$<0.1 at x<0.2), $D_{Li} \approx 0.8 D_{TFSI}$, and $D_{BMP} \approx 1.6 D_{TFSI}$. The main reason for the higher apparent lithium transference number in the mixture is the higher number density of lithium ions.

In order to further enhance the lithium transference number in such mixtures, the number density and/or the diffusion coefficient of the lithium ions have to be further increased relative to the other ions. A further increase of the Li− ion number density is generally believed to be very challenging since the mixtures tend to undergo salt crystallization or precipitation at high Li salt contents. The present invention has overcome this challenge. We have surprisingly observed that the addition of a very small proportion of a highly volatile organic liquid (e.g. an ether-based solvent) can significantly increase the solubility limit of some Li salt in a highly viscous liquefied gas, organic liquid (e.g. VC), or an ionic liquid (e.g. typically from x<0.2 to x>0.3-0.6, or from typically 1-2 M to >5 M). This can be achieved with an ionic liquid (or viscous organic liquid)-to-volatile organic solvent ratio as high as 10:1, hence, keeping the volatile solvent content to a bare minimum and minimizing the potential flammability of the electrolyte.

The diffusion coefficients of the ions, as measured in the pulsed field gradient NMR (PFG-NMR) experiments, depend on the effective radius of the diffusing entities. Due to the strong interactions between $Li^-$ ions and $TFSI^-$ ions, $Li^+$ ions can form $[Li(TFSI)_{n+1}]^{n-}$ complexes. Coordination numbers up to n+1=4 have been reported in open literature. The coordination number determines the effective hydrodynamic radius of the complex and thus the diffusion coefficient in the liquid mixture. The Stokes-Einstein equation, $Di=k_BT/(c\pi\eta r_i)$, may be used to calculate the effective hydrodynamic radius of a diffusing entity, ri, from its diffusion coefficient Di. The constant c varies between 4 and 6, depending on the shape of the diffusing entity. A comparison of the effective hydrodynamic radii of cations and anions in ionic liquids with their van der Waals radii reveals that the c values for cations are generally lower than for anions. In the case of EMI-TFSI/Li-TFSI mixtures, hydrodynamic radii for Li are in the range of 0.7-0.9 nm. This is approximately the van der Waals radius of $[Li(TFSI)_2]^-$ and $[Li(TFSI)_3]^{2-}$ complexes. In the case of the BMP-TFSI/Li-TFSI mixture with x=0.377, the effective hydrodynamic radius of the diffusing lithium complex is $r_{Li}=(D_{BMP}/D_{Li})r_{BMP}\approx 1.1$ nm, under the assumption that $r_{BMP}\approx 0.55$ nm and that the c values for $BMP^+$ and for the diffusing Li complex are identical. This value for $r_{Li}$ suggests that the lithium coordination number in the diffusing complex is at least 2 in the mixtures containing a low salt concentration.

Since the number of $TFSI^-$ ions is not high enough to form a significant amount of $[Li(TFSI)_3]^{2-}$ complexes, most lithium ions should be diffusing as $[Li(TFSI)_2]^-$ complexes. If, on the other hand, higher Li salt concentrations are achieved without crystallization (e.g. in our quasi-solid electrolytes), then the mixtures should contain a considerable amount of neutral [Li(TFSI)] complexes, which are smaller ($r_{[Li(TFSI)]}\approx 0.4$ nm) and should have higher diffusivities. Thus, a higher salt concentration would not only enhance the number density of lithium ions but should also lead to higher diffusion coefficients of the diffusing lithium complexes relative to the organic cations. The above analysis is applicable to electrolytes containing liquefied gas solvents, organic liquid solvents, or ionic liquid solvents (with or without the electrolyte additives). In all cases, when the lithium salt concentrations are higher than a threshold, there will be an increasing number of free or un-clustered $Li^+$ ions to move between the anode and the cathode when the concentration is further increased, providing adequate amount of $Li^+$ ions required for intercalation/de-intercalation or chemical reactions at the cathode and the anode. The presence of an additive selected from the list would favorably reduce the electrolyte flammability and would not negatively impact the transference number.

In addition to the non-flammability and high lithium ion transference numbers as discussed above, there are several additional benefits associated with using the presently invented quasi-solid electrolytes. As one example, the quasi-solid electrolyte can significantly enhance cyclic and safety performance of rechargeable lithium batteries through effective suppression of lithium dendrite growth. It is generally accepted that dendrites start to grow in the non-aqueous liquid electrolyte when the anion is depleted in the vicinity of the electrode where plating occurs. In the ultrahigh concentration electrolyte, there is a mass of anions to keep the balance of cations ($Li^+$) and anions near metallic lithium anode. Further, the space charge created by anion depletion is minimal, which is not conducive to dendrite growth. Furthermore, due to both ultrahigh lithium salt concentration and high lithium-ion transference number, the quasi-solid electrolyte provides a large amount of available lithium-ion flux and raises the lithium ionic mass transfer rate between the electrolyte and the lithium electrode, thereby enhancing the lithium deposition uniformity and dissolution during charge/discharge processes. Additionally, the local high viscosity induced by a high concentration will increase the pressure from the electrolyte to inhibit dendrite growth, potentially resulting in a more uniform deposition on the surface of the anode. The high viscosity could also limit anion convection near the deposition area, promoting more uniform deposition of Li ions. These reasons, separately or in combination, are believed to be responsible for the notion that no dendrite-like feature has been observed with any of the large number of rechargeable lithium cells (having salt concentration >2.5 M for Li—S cells) that we have investigated thus far. There is no dendrite problem associated with Li-ion cells or Li-ion sulfur cells where the anode does not have lithium metal as an anode active material. In these cases, a desirable salt concentration is from 1.5 M to 5.0 M and more preferably from 2.0 M to 3.5 M As another example of benefits, this electrolyte is capable of inhibiting lithium polysulfide dissolution at the cathode of a Li—S cell, thus overcoming the polysulfide shuttle phenomenon and allowing the cell capacity not to decay significantly with time. Consequently, a coulombic efficiency nearing 100% along with long cycle life has been achieved. The solubility of lithium polysulfide ($\xi$) is affected by the concentration of lithium ions already present in the electrolyte by the common ion effect. The solubility product ($K_{sp}$) of lithium polysulfide may be written as:

$$Li_2S_n \leftrightarrow 2Li^+ + S_n^{2-}; \quad K_{sp}=[Li^+]^2[S_n^{2-}]=4\xi_o^3; \quad \xi_o=(K_{sp}/4)^{1/3} \quad \text{(Eq. 4)},$$

where $\xi_o$ represents the solubility of lithium polysulfide when no lithium ion is present in the solvent. If the concentration of the lithium salt in the electrolyte (C) is significantly larger than the solubility of polysulfide, the solubility of polysulfide in the electrolyte containing the concentrated lithium salt can be expressed as:

$$\xi/\xi_o=(2\xi_o/C)^2 \quad \text{(Eq.5)}.$$

Therefore, when a concentrated electrolyte is used, the solubility of lithium polysulfide will be reduced significantly.

An embodiment of the present invention is a rechargeable lithium cell selected from a lithium metal secondary cell, a lithium-ion cell, a lithium-sulfur cell, a lithium-ion sulfur cell, or a lithium-air cell. The rechargeable lithium cell comprises a cathode having a cathode active material, an anode having an anode active material, an optional porous separator separating the anode and the cathode, a non-flammable quasi-solid electrolyte in contact with the cathode and the anode, wherein the electrolyte contains a lithium salt dissolved in a first liquefied gas solvent with a concentration sufficiently high so that the electrolyte exhibits a vapor pressure less than 0.01 kPa when measured at 20° C., a flash point at least 20 degrees Celsius higher than a flash point of said first organic liquid solvent alone, a flash point higher than 150° C., or no flash point, wherein the lithium salt concentration x is from 1.5 M to 5.0M and an electrolyte additive is added into the liquid solvent. The rechargeable lithium cell preferably contains a quasi-solid electrolyte having a lithium ion transference number greater than 0.3, preferably and typically greater than 0.4, and most preferably and typically greater than 0.6.

The preferred liquefied gas solvents include methane, fluoromethane, difluoromethane, chloromethane, dichloromethane, ethane, fluoroethane, difluoroethane, tetrafluoroethane, chloroethane, dichloroethane, tetrachloroethane, propane, fluoropropane, chloropropane, ethylene, fluoroethylene, chloroethylene, or a combination thereof.

The liquid additive may be selected from Hydrofluoro ether (HFE), Trifluoro propylene carbonate (FPC), Methyl nonafluorobutyl ether (MFE), Fluoroethylene carbonate (FEC), Tris(trimethylsilyl)phosphite (TTSPi), Triallyl phosphate (TAP), Ethylene sulfate (DTD), 1,3-propane sultone (PS), Propene sultone (PES), Diethyl carbonate (DEC), Alkylsiloxane (Si—O), Alkyylsilane (Si—C), liquid oligomeric silaxane (—Si—O—Si—), Ttetraethylene glycol dimethylether (TEGDME), canola oil, or a combination thereof.

The liquid additive or co-solvent may be selected from the group consisting of 1,3-dioxolane (DOL), 1,2-dimethoxy-ethane (DME), tetraethylene glycol dimethylether (TEGDME), poly(ethylene glycol) dimethyl ether (PEGDME), diethylene glycol dibutyl ether (DEGDBE), 2-ethoxyethyl ether (EEE), sulfone, sulfolane, ethylene carbonate (EC), dimethyl carbonate (DMC), methylethyl carbonate (MEC), diethyl carbonate (DEC), ethyl propionate, methyl propionate, propylene carbonate (PC), gamma.-butyrolactone (γ-BL), acetonitrile (AN), ethyl acetate (EA), propyl formate (PF), methyl formate (MF), toluene, xylene, methyl acetate (MA), fluoroethylene carbonate (FEC), vinylene carbonate (VC), allyl ethyl carbonate (AEC), a hydrofloroether (e.g. methyl perfluorobutyl ether, MFE, or ethyl perfluorobutyl ether, EFE), and combinations thereof.

The lithium salt may be selected from lithium perchlorate ($LiClO_4$), lithium hexafluorophosphate ($LiPF_6$), lithium borofluoride ($LiBF_4$), lithium hexafluoroarsenide ($LiAsF_6$), lithium trifluoro-metasulfonate ($LiCF_3SO_3$), bis-trifluoromethyl sulfonylimide lithium ($LiN(CF_3SO_2)_2$), lithium bis(oxalato)borate (LiBOB), lithium oxalyldifluoroborate ($LiBF_2C_2O_4$), lithium oxalyldifluoroborate ($LiBF_2C_2O_4$), lithium nitrate ($LiNO_3$), Li-Fluoroalkyl-Phosphates ($LiPF_3(CF_2CF_3)_3$), lithium bisperfluoro-ethysulfonylimide (LiBETI), lithium bis(trifluoromethanesulphonyl)imide, lithium bis(fluorosulphonyl)imide, lithium trifluoromethanesulfonimide (LiTFSI), an ionic liquid lithium salt, or a combination thereof.

The ionic liquid is composed of ions only. Ionic liquids are low melting temperature salts that are in a molten or liquid state when above a desired temperature. For instance, an ionic salt is considered as an ionic liquid if its melting point is below 100° C. If the melting temperature is equal to or lower than room temperature (25° C.), the salt is referred to as a room temperature ionic liquid (RTIL). The IL-based lithium salts are characterized by weak interactions, due to the combination of a large cation and a charge-delocalized anion. This results in a low tendency to crystallize due to flexibility (anion) and asymmetry (cation).

Some ILs may be used as a co-solvent (not as a salt) to work with the first organic solvent of the present invention. A well-known ionic liquid is formed by the combination of a 1-ethyl-3-methyl-imidazolium (EMI) cation and an N,N-bis(trifluoromethane)sulphonamide (TFSI) anion. This combination gives a fluid with an ionic conductivity comparable to many organic electrolyte solutions, a low decomposition propensity and low vapor pressure up to ~300-400° C. This implies a generally low volatility and non-flammability and, hence, a much safer electrolyte solvent for batteries.

Ionic liquids are basically composed of organic or inorganic ions that come in an unlimited number of structural variations owing to the preparation ease of a large variety of their components. Thus, various kinds of salts can be used to design the ionic liquid that has the desired properties for a given application. These include, among others, imidazolium, pyrrolidinium and quaternary ammonium salts as cations and bis(trifluoromethanesulphonyl) imide, bis(fluorosulphonyl)imide and hexafluorophosphate as anions. Useful ionic liquid-based lithium salts (not solvent) may be composed of lithium ions as the cation and bis(trifluoromethanesulphonyl)imide, bis(fluorosulphonyl)imide and hexafluorophosphate as anions. For instance, lithium trifluoromethanesulfonimide (LiTFSI) is a particularly useful lithium salt.

Based on their compositions, ionic liquids come in different classes that include three basic types: aprotic, protic and zwitterionic types, each one suitable for a specific application. Common cations of room temperature ionic liquids (RTILs) include, but are not limited to, tetraalkylammonium, di, tri, and tetra-alkylimidazolium, alkylpyridinium, dialkyl-pyrrolidinium, dialkylpiperidinium, tetraalkylphosphonium, and trialkylsulfonium. Common anions of RTILs include, but are not limited to, $BF_4^-$, $B(CN)_4^-$, $CH_3BF_3^-$, $CH_2CHBF_3^-$, $CF_3BF_3^-$, $C_2F_5BF_3^-$, n-$C_3F_7BF_3^-$, n-$C_4F_9BF_3^-$, $PF_6^-$, $CF_3CO_2^-$, $CF_3SO_3^-$, $N(SO_2CF_3)_2^-$, $N(COCF_3)(SO_2CF_3)^-$, $N(SO_2O_2)^-$, $N(CN)_2^-$, $C(CN)_3^-$, $SCN^-$, $SeCN^-$, $CuCl_2^-$, $AlCl_4^-$, $F(HF)_{2.3}^-$, etc. Relatively speaking, the combination of imidazolium- or sulfonium-based cations and complex halide anions such as $AlCl_4^-$, $BF_4^-$, $CF_3CO_2^-$, $CF_3SO_3^-$, $NTf_2^-$, $N(SO_2F)_2^-$, or $F(HF)_{2.3}^-$ results in RTILs with good working conductivities.

RTILs can possess archetypical properties such as high intrinsic ionic conductivity, high thermal stability, low volatility, low (practically zero) vapor pressure, non-flammability, the ability to remain liquid at a wide range of temperatures above and below room temperature, high polarity, high viscosity, and wide electrochemical windows. These properties, except for the high viscosity, are desirable attributes when it comes to using an RTIL as an electrolyte co-solvent in a rechargeable lithium cell.

The anode active material may contain, as an example, lithium metal foil or a high-capacity Si, Sn, or $SnO_2$ capable of storing a great amount of lithium. For Li—S cells, the cathode active material may contain pure sulfur (if the anode active material contains lithium), lithium polysulfide, or any sulfur containing compound, molecule, or polymer. If the cathode active material includes lithium-containing species (e.g. lithium polysulfide) when the cell is made, the anode active material can be any material capable of storing a large amount of lithium (e.g. Si, Ge, Sn, $SnO_2$, etc). For other lithium secondary cells, the cathode active materials can include a transition metal fluoride (e.g. MnF3, $FeF_3$, etc.), a transition metal chloride (e.g. $CuCl_2$), a transition metal dichalcogenide (e.g. $TiS_2$, $TaS_2$, and $MoS_2$), a transition metal trichalcogenide (e.g., $NbSe_3$), a transition metal oxide (e.g., $MnO_2$, $CoO_2$, an iron oxide, a vanadium oxide, etc.), or a combination thereof. The vanadium oxide may be selected from the group consisting of $VO_2$, $Li_xVO_2$, $V_2O_5$, $Li_xV_2O_5$, $V_3O_8$, $Li_xV_3O_8$, $Li_xV_3O_7$, $V_4O_9$, $Li_xV_4O_9$, $V_6O_{13}$, $Li_xV_6O_{13}$, their doped versions, their derivatives, and combinations thereof, wherein $0.1 < x < 5$.

The rechargeable lithium metal or lithium-ion cell featuring a liquefied gas solvent-based quasi-solid electrolyte containing a high lithium salt concentration may contain a cathode active material selected from, as examples, a layered compound $LiMO_2$, spinel compound $LiM_2O_4$, olivine compound $LiMPO_4$, silicate compound $Li_2MSiO_4$, Tavorite compound $LiMPO_4F$, borate compound $LiMBO_3$, or a combination thereof, wherein M is a transition metal or a mixture of multiple transition metals.

Typically, the cathode active materials are not electrically conducting. Hence, in one embodiment, the cathode active material may be mixed with a conductive filler such as carbon black (CB), acetylene black (AB), graphite particles, expanded graphite particles, activated carbon, mesoporous carbon, meso-carbon micro bead (MCMB), carbon nano-tube (CNT), carbon nano-fiber (CNF), graphene sheet (also referred to as nano graphene platelet, NGP), carbon fiber, or a combination thereof. These carbon/graphite/graphene materials may be made into a form of fabric, mat, or paper for supporting the cathode active material.

In a preferred embodiment, the nanoscaled filaments (e.g. CNTs, CNFs, and/or NGPs) are formed into a porous nano-structure that contains massive surfaces to support either the anode active material (e.g. Li or Si coating) or the cathode active material (e.g. sulfur, lithium polysulfide, vanadium oxide, $TiS_2$, etc). The porous nano-structure should have pores having a pore size preferably from 2 nm to 1 μm prior to being impregnated with sulfur or lithium polysulfide. The pore size is preferably in the range of 2 nm-50 nm, further preferably 2 nm-10 nm, after the pores are impregnated with sulfur or lithium polysulfide. These pores are properly sized to accommodate the electrolyte at the cathode side and to retain the cathode active material in the pores during repeated charges/discharges. The same type of nano-structure may be implemented at the anode side to support the anode active material.

In another preferred embodiment, the cathode active material consists of (a) exfoliated graphite worms that are interconnected to form a porous, conductive graphite flake network comprising pores having a size smaller than 100 nm; and (b) nanoscaled powder or coating of sulfur, sulfur compound, or lithium polysulfide disposed in the pores or coated on a graphite flake surface wherein the powder or coating is in contact with the electrolyte and has a dimension less than 100 nm. Preferably, the exfoliated graphite worm amount is in the range of 1% to 90% by weight and the amount of powder or coating is in the range of 99% to 10% by weight based on the total weight of exfoliated graphite worms and sulfur, sulfur compound, or lithium polysulfide combined which is measured or calculated when the cell is in a fully charged state. Preferably, the amount of the powder or coating of sulfur, sulfur compound, or lithium polysulfide is in the range of 70% to 95% by weight. Most preferably, the amount of the powder or coating of sulfur, sulfur compound, or lithium polysulfide is no less than 80% by weight.

The electrons coming from or going out through the external load or circuit must go through the conductive additives (in a conventional sulfur cathode) or a conductive framework (e.g. exfoliated graphite mesoporous structure or nano-structure of conductive nano-filaments) to reach the cathode active material. Since the cathode active material (e.g. sulfur, lithium polysulfide, vanadium oxide, etc) is a poor electronic conductor, the active material particle or coating must be as thin as possible to reduce the required electron travel distance.

Conventional Li—S cells typically have been limited to less than 70% by weight of sulfur in a composite cathode composed of sulfur and the conductive additive/support. Even when the sulfur content in the prior art composite cathode reaches or exceeds 70% by weight, the specific capacity of the composite cathode is typically significantly lower than what is expected based on theoretical predictions. For instance, the theoretical specific capacity of sulfur is 1,675 mAh/g. A composite cathode composed of 70% sulfur (S) and 30% carbon black (CB), without any binder, should be capable of storing up to 1,675×70%=1,172 mAh/g. Unfortunately, the actually observed specific capacity is typically less than 75% (often less than 50%) of what can be achieved. In other words, the active material utilization rate is typically less than 75% (or even <50%). This has been a major issue in the art of Li—S cells and there has been no solution to this problem. Most surprisingly, the implementation of exfoliated graphite worms as a conductive supporting material for sulfur or lithium polysulfide, coupled with an ionic liquid electrolyte at the cathode, has made it possible to achieve an active material utilization rate of typically >>80%, more often greater than 90%, and, in many cases, close to 99%.

In the presently invented lithium-sulfur cell, the pores of the porous sulfur/exfoliated graphite mixture or composite preferably have a size from 2 nm to 10 nm to accommodate electrolyte therein after the nanoscaled powder or coating of sulfur, sulfur compound, or lithium polysulfide is disposed in the pores or coated on the graphite flake surface. These pore sizes in the sulfur/exfoliated graphite mixture or composite are surprisingly capable of further suppressing, reducing, or eliminating the shuttle effect. Not wishing to be bound by the theory, but we feel that this is likely due to the unexpected capability of exfoliated graphite flake surfaces spaced 2-10 nm apart to retain lithium polysulfides in the minute pockets (pores) during the charge and discharge cycles. This ability of graphitic surfaces to prevent out-migration of lithium polysulfide is another big surprise to us.

The exfoliated graphite worms can be obtained from the intercalation and exfoliation of a laminar graphite material. The conventional process for producing exfoliated graphite worms typically begins with subjecting a graphitic material to a chemical treatment (intercalation and/or oxidation using a strong acid and/or oxidizing agent) to form a graphite intercalation compound (GIC) or graphite oxide (GO). This is most often accomplished by immersing natural graphite powder in a mixture of sulfuric acid, nitric acid (an oxidizing agent), and another oxidizing agent (e.g. potassium permanganate or sodium chlorate). The resulting GIC is actually some type of graphite oxide (GO) particles. This GIC is then repeatedly washed and rinsed in water to remove excess acids, resulting in a graphite oxide suspension or dispersion, which contains discrete and visually discernible graphite oxide particles dispersed in water. There are different processing routes that can be followed after this rinsing step to form different types of graphite or graphene products.

For instance, a first route involves removing water from the suspension to obtain "expandable graphite," which is essentially a mass of dried GIC or dried graphite oxide particles. Upon exposure of expandable graphite to a temperature in the range of typically 800-1,050° C. for approximately 30 seconds to 2 minutes, the GIC undergoes a rapid expansion by a factor of 30-800 to form "graphite worms", which are each a collection of exfoliated, but largely unseparated or still interconnected graphite flakes.

As a second route, one may choose to use a low-intensity air mill or shearing machine to simply break up the graphite worms for the purpose of producing the so-called "expanded graphite flakes," which are isolated and separated graphite flakes or platelets thicker than 100 nm (hence, not a nano material by definition). Alternatively, exfoliated graphite worms may be the re-compressed (e.g. roll-pressed) to form flexible graphite sheet or flexible graphite foil that is essentially a solid film not permeable to battery electrolyte. Such an electrolyte-impermeable film can be a good battery current collector (e.g. to replace aluminum foil), but it does not have a sufficient amount of specific surface area to support sulfur.

Alternatively, as a third route, the exfoliated graphite worms may be subjected to high-intensity mechanical shearing (e.g. using an ultrasonicator, high-shear mixer, high-intensity air jet mill, or high-energy ball mill) to form separated single-layer and/or multi-layer graphene sheets (collectively called nano graphene platelets or NGPs), as disclosed in our U.S. application Ser. No. 10/858,814. Single-layer graphene can be as thin as 0.34 nm, while multi-layer graphene can have a thickness up to 100 nm.

The graphite oxide suspension (after a sufficiently high degree of oxidation) may be subjected to ultrasonication for the purpose of separating/isolating individual graphene oxide sheets from graphite oxide particles. This is based on the notion that the inter-graphene plane separation bas been increased from 0.335 nm in natural graphite to 0.6-1.1 nm in highly oxidized graphite oxide, significantly weakening the van der Waals forces that hold neighboring planes together. Ultrasonic power can be sufficient to further separate graphene plane sheets to form separated, isolated, or discrete graphene oxide (GO) sheets having an oxygen content of typically 20-50% by weight. These graphene oxide sheets can then be chemically or thermally reduced to obtain "reduced graphene oxides" (RGO) typically having an oxygen content of 0.01%-10% by weight, more typically 0.01%-5% by weight, and most typically 0.01%-2% by weight.

In general, NGPs include single-layer and multi-layer graphene or reduced graphene oxide with an oxygen content of 0-10% by weight, more typically 0-5% by weight, and preferably 0-2% weight. Pristine graphene has essentially 0% oxygen. Graphene oxide (including RGO) can have 0.01%-50% by weight of oxygen.

As indicated earlier, dried GIC or GO powder may be exposed a thermal shock (at a high temperature, typically 800-1,050° C.) for a short period of time (typically 30-120 seconds), allowing the constituent graphite flakes to freely expand. The resulting graphite worms typically have an expanded volume that is 30 to 800 times higher than the original graphite volume, depending upon the degree of oxidation or intercalation.

Typically, an oxygen content between 46-50% by weight based on the total GO weight is an indication of practically complete oxidation of graphite, which is also reflected by the complete disappearance of the X-ray diffraction curve peak originally located at 2θ=approximately 26 degrees for un-intercalated or un-oxidized natural graphite. This diffraction peak at 2θ=approximately 26 degrees corresponds to the $d_{002}$ spacing between two (002) graphene planes.

Acids, such as sulfuric acid, are not the only type of intercalating agent (intercalant) that penetrate into spaces between graphene planes. Many other types of intercalating agents, such as alkali metals (Li, K, Na, Cs, and their alloys or eutectics), can be used to intercalate graphite to stage 1, stage 2, stage 3, etc. Stage n implies one intercalant layer for every n graphene planes. For instance, a stage-1 potassium-intercalated GIC means there is one layer of K for every graphene plane; or, one can find one layer of K atoms inserted between two adjacent graphene planes in a G/K/G/K/G/KG . . . sequence, where G is a graphene plane and K is a potassium atom plane. A stage-2 GIC will have a sequence of GG/K/GG/K/GG/K/GG . . . and a stage-3 GIC will have a sequence of GGG/K/GGG/K/GGG . . . , etc.

A graphite worm is characterized as having a network of largely interconnected exfoliated graphite flaks with pores between flakes. The flakes have a typical length or width dimension of 0.5-100 µm (more typically 1-20 µm), depending upon the types of starting graphitic materials used and these lateral dimensions (length or width) are relatively independent of the GIC stage number (or oxygen content in GO), the exfoliation temperature, and the exfoliation environment. However, these factors have major impact on the volume expansion ratio (exfoliated graphite worm volume vs. starting graphite particle volume), flake thickness range, and pore size range of exfoliated graphite worms.

For instance, Stage-1 GIC or fully oxidized graphite (GO with 40-50% oxygen content), upon un-constrained exfoliation at 1,000° C. for one minute, exhibit a typical volume expansion ratio of approximately 450-800%, flake thickness range of 0.34 to 3 nm, and pore size range of 50 nm to 20 µm. By contrast, Stage-5 GIC or GO with 20-25% oxygen content, upon un-constrained exfoliation at 1,000° C. for one minute, exhibit a volume expansion ratio of approximately 80-180%, flake thickness range of 1.7 to 200 nm, and pore size range of 30 nm to 2 µm.

Stage-1 GIC is the most desirable since it leads to highly exfoliated graphite worms featuring thin graphite flakes with very high specific surface areas (typically >500 m$^2$/g, often >700 m$^2$/g, and even >1,000 m$^2$/g in several cases). Higher surface areas make it possible to deposit thinner sulfur or lithium polysulfide coating given the same sulfur or lithium polysulfide volume. Consequently, there is significantly reduced proportion of thicker coating of sulfur or lithium polysulfide attached to the exfoliated graphite flake surfaces. This could allow most of the sulfur to be accessible to the lithium ions during the cell discharge.

The flakes in an exfoliated graphite worm remain substantially interconnected (physically in contact with each other or bonded to each other), forming a network of electron-conducting paths. Hence, the electrical conductivity of the graphite worms is relatively high (10-10,000 S/cm), which can be orders of magnitude higher than that of carbon black, activated carbon, polymeric carbon, amorphous carbon, hard carbon, soft carbon, and meso-phase pitch, etc.

The soft and fluffy worms, upon impregnation or coating with sulfur, have exhibited an unexpected improvement in mechanical strength (e.g. compression strength or bending strength) by up to 2-3 orders of magnitude. The impregnated graphite worms may be re-compressed to increase their physical density and structural integrity, if deemed necessary. Graphite worm-sulfur composites have a density typically in the range of 0.02 g/cm$^3$ to 1.0 g/cm$^3$, depending upon the degree of exfoliation and the condition of re-compression.

When the cathode is made, the cathode active material (sulfur, lithium polysulfide, vanadium oxide, titanium disulfide, etc) is embedded in the nanoscaled pores constituted by the exfoliated graphite flakes. Preferably, the cathode active material is grinded into nanometer scale (preferably <10 nm and more preferably <5 nm). Alternatively, the cathode active material may be in a thin-film coating form deposited on surfaces of the graphite flakes obtained by melt impregnation, solution deposition, electro-deposition, chemical vapor deposition (CVD), physical vapor deposition, sputtering, laser ablation, etc. This coating is then brought in contact with electrolyte before, during, or after the cathode is made, or even after the cell is produced.

The present design of a mesoporous graphite worm cathode with meso-scaled pores in a Li—S cell was mainly motivated by the notion that a significant drawback with cells containing cathodes comprising elemental sulfur, organosulfur and carbon-sulfur materials is related to the dissolution and excessive out-diffusion of soluble sulfides, polysulfides, organo-sulfides, carbon-sulfides and/or carbon-polysulfides (anionic reduction products) from the cathode into the rest (anode, in particular) of the cell. This process leads to several problems: high self-discharge rates, loss of cathode capacity, corrosion of current collectors and electrical leads leading to loss of electrical contact to active cell components, fouling of the anode surface giving rise to malfunction of the anode, and clogging of the pores in the cell membrane separator which leads to loss of ion transport and large increases in internal resistance in the cell.

At the anode side, when lithium metal is used as the sole anode active material in a Li metal cell, there is concern about the formation of lithium dendrites, which could lead to internal shorting and thermal runaway. Herein, we have used two approaches, separately or in combination, to addressing this dendrite formation issue: one involving the use of a high-concentration electrolyte and the other the use of a nano-structure composed of conductive nano-filaments. For the latter, multiple conductive nano-filaments are processed to form an integrated aggregate structure, preferably in the form of a closely packed web, mat, or paper, characterized in that these filaments are intersected, overlapped, or somehow bonded (e.g., using a binder material) to one another to form a network of electron-conducting paths. The integrated structure has substantially interconnected pores to accommodate electrolyte. The nano-filament may be selected from, as examples, a carbon nanofiber (CNF), graphite nanofiber (GNF), carbon nanotube (CNT), metal nanowire (MNW), conductive nanofibers obtained by electro-spinning, conductive electro-spun composite nanofibers, nanoscaled graphene platelet (NGP), or a combination thereof. The nano-filaments may be bonded by a binder material selected from a polymer, coal tar pitch, petroleum pitch, mesophase pitch, coke, or a derivative thereof.

Surprisingly and significantly, the nano-structure provides an environment that is conducive to uniform deposition of lithium atoms, to the extent that no geometrically sharp structures or dendrites were found in the anode after a large number of cycles. Not wishing to be bound by any theory, but the applicants envision that the 3-D network of highly conductive nano-filaments provide a substantially uniform attraction of lithium ions back onto the filament surfaces during re-charging. Furthermore, due to the nanometer sizes of the filaments, there is a large amount of surface area per unit volume or per unit weight of the nano-filaments. This ultra-high specific surface area offers the lithium ions an opportunity to uniformly deposit a lithium metal coating on filament surfaces at a high rate, enabling high re-charge rates for a lithium metal secondary battery.

The presently invented high-concentration electrolyte system and optional mesoporous exfoliated graphite-sulfur may be incorporated in several broad classes of rechargeable lithium cells. In the following examples, sulfur or lithium polysulfide is used as a cathode active material for illustration purposes:

(A) Lithium metal-sulfur with a conventional anode configuration: The cell contains an optional cathode current collector, a cathode (containing a composite of sulfur or lithium polysulfide and a conductive additive or a conductive supporting framework, such as a mesoporous exfoliated graphite or a nano-structure of conductive nano-filaments), a separator/electrolyte (featuring the gradient electrolyte system), and an anode current collector. Potential dendrite formation may be overcome by using the high-concentration electrolyte at the anode.

(B) Lithium metal-sulfur cell with a nano-structured anode configuration: The cell contains an optional cathode current collector, a cathode (containing a composite of sulfur or lithium polysulfide and a conductive additive or a conductive supporting framework, such as a mesoporous exfoliated graphite or a nano-structure of conductive nano-filaments), a separator/electrolyte (featuring the gradient electrolyte system), an optional anode current collector, and a nano-structure to accommodate lithium metal that is deposited back to the anode during a charge or re-charge operation. This nano-structure (web, mat, or paper) of nano-filaments provide a uniform electric field enabling uniform Li metal deposition, reducing the propensity to form dendrites. This configuration, coupled with the high-concentration electrolyte at the anode, provides a dendrite-free cell for a long and safe cycling behavior.

(C) Lithium ion-sulfur cell with a conventional anode: For instance, the cell contains an anode composed of anode active graphite particles bonded by a binder, such as polyvinylidene fluoride (PVDF) or styrene-butadiene rubber (SBR). The cell also contains a cathode current collector, a cathode (containing a composite of sulfur or lithium polysulfide and a conductive additive or a conductive supporting framework, such as a mesoporous exfoliated graphite or a nano-structure of conductive nano-filaments), a separator/electrolyte (featuring the quasi-solid electrolyte system), and an anode current collector; and (D) Lithium ion-sulfur cell with a nano-structured anode: For instance, the cell contains a web of nano-fibers coated with Si coating or bonded with Si nano particles. The cell also contains an optional cathode current collector, a cathode (containing a composite of sulfur or lithium polysulfide and a conductive additive or a conductive supporting framework, such as a mesoporous exfoliated graphite or a nano-structure of conductive nano-filaments), a separator/electrolyte (featuring the quasi-solid electrolyte system), and an anode current collector. This configuration provides an ultra-high capacity, high energy density, and a safe and long cycle life.

This sulfur or lithium polysulfide in (A)-(D) can be replaced with any other type of cathode active materials, such as a transition metal dichalcogenide (e.g., $TiS_2$), transition metal trichalcogenide (e.g., $NbSe_3$), transition metal oxide (e.g., $MnO_2$, a vanadium oxide, etc), a layered compound $LiMO_2$, spinel compound $LiM_2O_4$, olivine compound $LiMPO_4$, silicate compound $Li_2MSiO_4$, Tavorite compound $LiMPO_4F$, borate compound $LiMBO_3$, or a combination thereof, wherein M is a transition metal or a mixture of multiple transition metals In the lithium-ion sulfur cell (e.g. as described in (C) and (D) above), the anode active material can be selected from a wide range of high-capacity materials, including (a) silicon (Si), germanium (Ge), tin (Sn), lead (Pb), antimony (Sb), bismuth (Bi), zinc (Zn), aluminum (Al), nickel (Ni), cobalt (Co), manganese (Mn), titanium (Ti), iron (Fe), and cadmium (Cd), and lithiated versions thereof; (b) alloys or intermetallic compounds of Si, Ge, Sn, Pb, Sb, Bi, Zn, Al, or Cd with other elements, and lithiated versions thereof, wherein said alloys or compounds are stoichiometric or non-stoichiometric; (c) oxides, carbides, nitrides, sulfides, phosphides, selenides, and tellurides of Si, Ge, Sn, Pb, Sb, Bi, Zn, Al, Fe, Ni, Co, Ti, Mn, or Cd, and their mixtures or composites, and lithiated versions thereof; (d) salts and hydroxides of Sn and lithiated versions thereof; (e) carbon or graphite materials and prelithiated versions thereof; and combinations thereof. Non-lithiated versions may be used if the cathode side contains lithium polysulfides or other lithium sources when the cell is made.

A possible lithium metal cell may be comprised of an anode current collector, an electrolyte phase (optionally but preferably supported by a porous separator, such as a porous polyethylene-polypropylene co-polymer film), a mesoporous exfoliated graphite worm-sulfur cathode of the instant invention (containing a cathode active material), and an optional cathode collector. This cathode current collector is optional because the presently invented mesoporous exfoliated graphite structure, if properly designed, can act as a current collector or as an extension of a current collector.

To achieve high capacity in a battery, it is desirable to have either a higher quantity or loading of the cathode active material or, preferably, a higher-capacity cathode active material in the cathode layer. Lithium and sulfur are highly desirable as the electrochemically active materials for the anode and cathode, respectively, because they provide nearly the highest energy density possible on a weight or volume basis of any of the known combinations of active materials (other than the Li-air cell). To obtain high energy densities, the lithium can be present as the pure metal, in an alloy (in a lithium-metal cell), or in an intercalated form (in a lithium-ion cell), and the sulfur can be present as elemental sulfur or as a component in an organic or inorganic material with a high sulfur content.

With sulfur-based compounds, which have much higher specific capacities than the transition metal oxides of lithium-ion cells, it is difficult to achieve efficient electrochemical utilization of the sulfur-based compounds at high volumetric densities because the sulfur-based compounds are highly insulating and are generally not micro-porous. For example, U.S. Pat. No. 5,532,077 to Chu describes the problems of overcoming the insulating character of elemental sulfur in composite cathodes and the use of a large volume fraction of an electronically conductive material (carbon black) and of an ionically conductive material (e.g., polyethylene oxide or PEO) in the composite electrode to try to overcome these problems. Typically, Chu had to use nearly 50% or more of non-active materials (e.g., carbon black, binder, PEO, etc), effectively limiting the relative amount of active sulfur. Furthermore, presumably one could choose to use carbon paper (instead of or in addition to carbon black) as a host for the cathode active material. However, this conventional carbon fiber paper does not allow a sufficient amount of cathode active material to be coated on the large-diameter carbon fiber surface yet still maintaining a low coating thickness, which is required of a reduced lithium diffusion path length for improved charge/discharge rates and reduced resistance. In other words, in order to have a reasonable proportion of an electrode active material coated on a large-diameter fiber, the coating thickness has to be proportionally higher. A thicker coating would mean a longer diffusion path for lithium to come in and out, thereby slowing down the battery charge/discharge rates. The instant application solved these challenging problems by using an integrated 3-D mesoporous graphite worm structure consisting of nano-thickness exfoliated graphite flakes having massive conductive surfaces to host the cathode active material (sulfur, sulfur-containing compound, or lithium polysulfide).

As opposed to carbon paper (often used as a host for elemental sulfur, conductive additives, ion conductors, and electrolyte) that was composed of micron-scaled carbon fibers (typically having a diameter of >12 µm), the instant application makes use of graphite worms of nano-thickness flakes with a thickness less than 200 nm, preferably and more typically less than 100 nm, even more preferably and more typically less than 10 nm, and most preferably and more typically less than 3 nm. The exfoliated graphite worms have been ignored or overlooked by the workers in the art of designing electrodes likely due to the notion that these worms are perceived as too weak to be handled in an electrode-making process and too weak to support any sulfur-containing electrode active material. Indeed, graphite worms are extremely weak. However, impregnation of coating of graphite worms with sulfur or sulfur compounds significantly enhances the mechanical strength of graphite worms, to the extent that the resulting composite materials can be readily formed into a cathode using a conventional battery electrode-making machine (coater). Further, there has been no teaching that exfoliated graphite worms could be used to confine lithium polysulfide and preventing lithium polysulfide from migrating out of the cathode and entering the anode. This was not trivial or obvious to one of ordinary skills in the art.

The interconnected network of exfoliated graphite worms forms a continuous path for electrons, resulting in significantly reduced internal energy loss or internal heating for either the anode or the cathode (or both). This network is electronically connected to a current collector and, hence, all graphite flakes that constitute graphite worms are essentially connected to the current collector. In the instant invention, the lithium sulfide coating is deposited on flake surfaces and, even if the coating were to fracture into separate segments, individual segments would still remain in physical contact with the underlying flakes, which is essentially part of the current collector. The electrons transported to the cathode can be distributed to all cathode active coatings. In the case of lithium sulfide particles dispersed/dissolved in an electrolyte inside meso pores of the cathode structure, the particles are necessarily nanoscaled (the salt-electrolyte solution pool also nanoscaled) and, hence, are conducive to fast cathode reaction during the charging operation.

The lithium metal cell of the instant application can have a nano-structured anode or a more conventional anode structure, although such a conventional structure is not preferred. In a more conventional anode structure, acetylene black, carbon black, or ultra-fine graphite particles may be used as a conductive additive. The binder may be chosen from polytetrafluoroethylene (PTFE), polyvinylidene fluoride (PVDF), ethylene-propylene-diene copolymer (EPDM), or styrene-butadiene rubber (SBR), for example. Conductive materials such as electronically conductive polymers, meso-phase pitch, coal tar pitch, and petroleum pitch may also be used as a binder. Preferable mixing ratio of these ingredients may be 80 to 95% by weight for the anode active material (natural or artificial graphite particles, MCMBs, coke-based anode particles, carbon-coated Si nano particles, etc), 3 to 20% by weight for the conductive additive, and 2 to 7% by weight for the binder. The anode current collector may be selected from copper foil or stainless steel foil. The cathode current collector may be an aluminum foil or a nickel foil. There is no particularly significant restriction on the type of current collector, provided the material is a good electrical conductor and relatively corrosion resistant. The separator may be selected from a polymeric nonwoven fabric, porous polyethylene film, porous polypropylene film, or porous PTFE film.

The most important property of a filament herein used to support an electrode active material (e.g. Li or Si at the anode) is a high electrical conductivity to enable facile transport of electrons with minimal resistance. A low conductivity implies a high resistance and high energy loss, which is undesirable. The filament should also be chemically and thermo-mechanically compatible with the intended active material (i.e., lithium at the anode) to ensure a good contact between the filament and the coating upon repeated charging/discharging and heating/cooling cycles. Several techniques can be employed to fabricate a conductive aggregate of filaments (a web or mat), which is a monolithic body having desired interconnected pores. In one preferred embodiment of the present invention, the porous web can be made by using a slurry molding or a filament/binder spraying technique. These methods can be carried out in the following ways:

EXAMPLES

In the examples discussed below, unless otherwise noted, raw materials such as silicon, germanium, bismuth, antimony, zinc, iron, nickel, titanium, cobalt, and tin were obtained from either Alfa Aesar of Ward Hill, Mass., Aldrich Chemical Company of Milwaukee, Wis. or Alcan Metal Powders of Berkeley, Calif. X-ray diffraction patterns were collected using a diffractometer equipped with a copper target x-ray tube and a diffracted beam monochromator. The presence or absence of characteristic patterns of peaks was observed for each of the alloy samples studied. For example, a phase was considered to be amorphous when the X-ray diffraction pattern was absent or lacked sharp, well-defined peaks. In several cases, scanning electron microscopy (SEM) and transmission electron microscopy (TEM) were used to characterize the structure and morphology of the hybrid material samples.

A nano-structured cathode, comprising exfoliated graphite worm-sulfur (or polysulfide), was bonded onto an aluminum foil (a current collector). After solvent removal, web-aluminum foil configuration was hot-pressed to obtain a cathode or, alternatively, a complete cell was fabricated by laminating an anode current collector (Cu foil), an anode layer (e.g., a piece of Li foil, a nano-structured web with Si coating, or graphite particles bonded by PVDF), an electrolyte-separator layer, a mesoporous cathode, and a cathode current collector (e.g., stainless steel foil or aluminum foil) all at the same time. In some cases, an NGP-containing resin was used as a binder, for instance, between a cathode layer and a cathode current collector. Filaments may also be bonded by an intrinsically conductive polymer as a binder to form a web. For instance, polyaniline-maleic acid-dodecyl hydrogensulfate salt may be synthesized directly via emulsion polymerization pathway using benzoyl peroxide oxidant, sodium dodecyl sulfate surfactant, and maleic acid as dopants. Dry polyaniline-based powder may be dissolved in DMF up to 2% w/v to form a solution.

The conventional cathode of a Li—S cell was prepared in the following way. As an example, 60-80% by weight of lithium sulfide powder, 3.5% by weight of acetylene black, 13.5-33.5% by weight of graphite, and 3% by weight of ethylene-propylene-diene monomer powder were mixed together with toluene to obtain a mixture. The mixture was then coated on an aluminum foil (30 μm) serving as a current collector. The resulting two-layer aluminum foil-active material configuration was then hot-pressed to obtain a positive electrode. In the preparation of a cylindrical cell, a positive electrode, a separator composed of a porous polyethylene film, and a negative electrode was stacked in this order. The stacked body was spirally wound with a separator layer being disposed at the outermost side to obtain an electrode assembly. For Li-ion cells were similarly made wherein, for instance, the cathode is prepared by mixing 90% by weight of a selected cathode active material with 5% conductive additive (e.g. carbon black), and 5% binder (e.g. PVDF).

The following examples are presented primarily for the purpose of illustrating the best mode practice of the present invention, not to be construed as limiting the scope of the present invention.

Example 1

Some Examples of Electrolytes Used

A wide range of lithium salts can be used as the lithium salt dissolved in an organic liquid solvent (alone or in a mixture with another organic liquid or an ionic liquid). The following are good choices for lithium salts that tend to be dissolved well in selected organic or ionic liquid solvents: lithium borofluoride ($LiBF_4$), lithium trifluoro-metasulfonate ($LiCF_3SO_3$), lithium bis-trifluoromethyl sulfonylimide ($LiN(CF_3SO_2)_2$ or LITFSI), lithium bis(oxalato) borate (LiBOB), lithium oxalyldifluoroborate ($LiBF_2C_2O_4$), and lithium bisperfluoroethy-sulfonylimide (LiBETI). A good electrolyte additive for helping to stabilize Li metal is $LiNO_3$. Particularly useful ionic liquid-based lithium salts include: lithium bis(trifluoro methanesulfonyl)imide (LiTFSI).

Preferred liquefied gases include methane, fluoromethane, difluoromethane, chloromethane, dichloromethane, ethane, fluoroethane, difluoroethane, tetrafluoroethane, chloroethane, dichloroethane, tetrachloroethane, propane, fluoropropane, chloropropane, ethylene, fluoroethylene, and chloroethylene.

Preferred volatile liquid co-solvents include: ethylene carbonate (EC), dimethyl carbonate (DMC), methylethyl carbonate (MEC), diethyl carbonate (DEC), propylene carbonate (PC), acetonitrile (AN), vinylene carbonate (VC), allyl ethyl carbonate (AEC), 1,3-dioxolane (DOL), and 1,2-dimethoxyethane (DME).

Preferred liquid electrolyte additives are Hydrofluoro ether (HFE), Trifluoro propylene carbonate (FPC), Methyl nonafluorobutyl ether (MFE), Fluoroethylene carbonate (FEC), Tris(trimethylsilyl)phosphite (TTSPi), Triallyl phosphate (TAP), Ethylene sulfate (DTD), 1,3-propane sultone (PS), Propene sultone (PES), Diethyl carbonate (DEC), Alkylsiloxane (Si—O), Alkyylsilane (Si—C), liquid oligomeric silaxane (—Si—O—Si—), and Ttetraethylene glycol dimethylether (TEGDME).

Preferred ionic liquid solvents may be selected from a room temperature ionic liquid (RTIL) having a cation selected from tetraalkylammonium, di-alkylimidazolium, alkylpyridinium, dialkyl-pyrrolidinium, or dialkylpiperidinium. The counter anion is preferably selected from $BF_4^-$, $B(CN)_4^-$, $CF_3CO_2^-$, $CF_3SO_3^-$, $N(SO_2CF_3)_2^-$, $N(COCF_3)$ $(SO_2CF_3)^-$, or $N(SO_2F)_2^-$. Particularly useful ionic liquid-based solvents include N-n-butyl-N-ethylpyrrolidinium bis (trifluoromethane sulfonyl)imide (BEPyTFSI), N-methyl-N-propylpiperidinium bis(trifluoromethyl sulfonyl)imide (PP$_{13}$TFSI), and N,N-diethyl-N-methyl-N-(2-methoxyethyl) ammonium bis(trifluorotnethylsulfonyl)imide.

Example 2

Vapor Pressure of Some Solvents and Corresponding Quasi-Solid Electrolytes with Various Lithium Salt Molecular Ratios Vapor pressures of several liquefied gas solvents (with or without a co-solvent) before and after adding a wide molecular ratio range of lithium salts, such as lithium borofluoride (LiBF$_4$), lithium trifluoro-metasulfonate (LiCF$_3$SO$_3$), or bis(trifluoro methanesulfonyl)imide (LiTFSI), and a broad array of electrolyte additives were measured. Some of the vapor pressure ratio data (p$_s$/p=vapor pressure of solution/vapor pressure of solvent alone) are plotted as a function of the lithium salt molecular ratio x, as shown in FIG. 1-FIG. 4, along with a curve representing the Raoult's Law. In most of the cases, the vapor pressure ratio follows the theoretical prediction based on Raoult's Law for up to x<0.15 only, above which the vapor pressure deviates from Raoult's Law in a novel and unprecedented manner. It appears that the vapor pressure drops at a very high rate when the molecular ratio x exceeds 0.2, and rapidly approaches a minimal or essentially zero when x exceeds 0.4. With a very low p$_s$/p value, the vapor phase of the electrolyte either cannot ignite or cannot sustain a flame for longer than 3 seconds once initiated. More significantly, by adding some amount of the selected additive, one can significantly shift the threshold concentration for non-flammability down to approximately 1.5 M or x=0.12.

Example 3

Flash Points and Vapor Pressure of Some Solvents and Additives and Corresponding Quasi-Solid Electrolytes with a Lithium Salt Molecular Ratio of x=0.2

The flash points of several solvents (with or without a liquid additive) and their electrolytes having a lithium salt molecular ratio x=0.2 are presented in Table 1 below. It may be noted that, according to the OSHA (Occupational Safety & Health Administration) classification, any liquid with a flash point below 35.7° C. is flammable. However, in order to ensure safety, we have designed our quasi-solid electrolytes to exhibit a flash point significantly higher than 38.7° C. (by a large margin, e.g. at least increased by 50° and preferably above 150° C.). The data in Table 1 indicate that the addition of a lithium salt to a molecular ratio of 0.2 is normally sufficient to meet these criteria provided a selective additive is added into the liquid solvent.

TABLE 1

The flash points and vapor pressures of select solvents and their electrolytes with a lithium salt molecular ratio x = 0.2 (approximately 2.5M).

| Liquid solvent | Flash point (° C.) | Liquid additive (additive/solvent = 25/75) | Flash point (° C.) with x = 0.2 of (Li salt) |
| --- | --- | --- | --- |
| Methane (bp = −188° C.) | <0 | none | <100 (LiBF$_4$) |
| Methane | | TEGDME | >150 (LiBF$_4$) |
| Fluoromethane | <25 | None | <150 (LiCF$_3$SO$_3$) |
| Fluoromethane | | Ethylene sulfate (DTD) | 155 (LiCF$_3$SO$_3$) |
| Ethane (bp = −135° C.) | <0 | none | 120 (LiCF$_3$SO$_3$) |
| Ethane | | FPC (Trifluoro propylene carbonate) | >200 (LiCF$_3$SO$_3$) |
| Fluoroethane | 33 | none | 95 (LiCF$_3$SO$_3$) |
| Fluoroethane | | FEC | >200 (LiCF$_3$SO$_3$) |
| Propane | <0 | none | 90 (LiBOB) |
| Propane | | MFE | >200 (LiBOB) |
| Fluoropropane | <20 | none | 85 (LiBF$_4$) |
| Fluoropropane | | 1,3-propane sultone (PS) | 150 (LiBF$_4$) |
| Ethylene | <0 | none | <100 (LiBF$_4$) |
| Ethylene | <0 | FEC | >150 (LiBF$_4$) |
| Chloropropane | <0 | none | >150 (LiBF$_4$) |
| Chloropropane | <0 | Triallyl phosphate (TAP) | >180(LiPF$_6$) |

*As per OSHA (Occupational Safety & Health Administration) classification, any liquid with a flash point below 38.7° C. is flammable.

Example 4

Lithium Ion Transference Numbers in Several Electrolytes

The Li$^-$ ion transference numbers of several types of electrolytes in relation to the lithium salt molecular ratio were studied and representative results are summarized in FIG. 5 to FIG. 7. In general, the Li$^+$ ion transference number in low salt concentration electrolytes decreases with increasing concentration from x=0 to x=0.2-0.35. However, beyond molecular ratios of x=0.2-0.35, the transference number increases with increasing salt concentration, indicating a fundamental change in the Li$^+$ ion transport mechanism. This was explained in the theoretical sub-sections earlier. Additionally, the incorporation of a select liquid additive to the electrolyte does not negatively impact the lithium ion transport behavior. In some cases, the liquid additive actually increases the transference number.

When Li$^+$ ions travel in a low salt concentration electrolyte (e.g. x<0.2), a Li$^+$ ion can drags multiple solvating anions or molecules along with it. The coordinated migration of such a cluster of charged species can be further impeded if the fluid viscosity is increased due to more salt dissolved in the solvent. In contrast, when an ultra-high concentration of lithium salt with x>0.2 is present, Li$^+$ ions could significantly out-number the available solvating anions that otherwise could cluster the lithium ions, forming multi-ion complex species and slowing down their diffusion process. This high Li$^+$ ion concentration makes it possible to have more "free Li$^+$ ions" (non-clustered), thereby providing a higher Li$^+$ transference number (hence, a facile Li$^+$ transport). The lithium ion transport mechanism changes from a multi-ion complex-dominating one (with an overall larger hydrodynamic radius) to single ion-dominating one (with a smaller hydrodynamic radius) having a large number of available free Li$^+$ ions. This observation has further asserted that an adequate number of Li$^+$ ions can quickly move through or from the liquefied gas-based quasi-solid electrolytes to make themselves readily available to interact or react with a cathode (during discharge) or an anode (during charge), thereby ensuring a good rate capability of a lithium secondary cell. Most significantly, these concentrated electrolytes are non-flammable and safe. The presence of a select liquid additive can decrease the required lithium salt concentration to make a non-flammable electrolyte and maintain the liquid flowability for electrolyte injection into the dry battery cells. Combined safety, facile lithium ion transport, good electrochemical performance characteristics, and ease of battery production have been thus far difficult to come by for all types of lithium secondary battery.

Example 5

Exfoliated Graphite Worms from Natural Graphite Using Hummers Method

Graphite intercalation compound (GIC) was prepared by intercalation and oxidation of natural graphite flakes (original size of 200 mesh, from Huadong Graphite Co., Pingdu, China, milled to approximately 15 μm) with sulfuric acid, sodium nitrate, and potassium permanganate according to the method of Hummers [U.S. Pat. No. 2,798,878, Jul. 9, 1957]. In this example, for every 1 gram of graphite, we used a mixture of 22 ml of concentrated sulfuric acid, 2.8 grams of potassium permanganate, and 0.5 grams of sodium nitrate. The graphite flakes were immersed in the mixture solution and the reaction time was approximately three hours at 30° C. It is important to caution that potassium permanganate should be gradually added to sulfuric acid in a well-controlled manner to avoid overheat and other safety issues. Upon completion of the reaction, the mixture was poured into deionized water and filtered. The sample was then washed repeatedly with deionized water until the pH of the filtrate was approximately 5. The slurry was spray-dried and stored in a vacuum oven at 60° C. for 24 hours. The resulting GIC was exposed to a temperature of 1,050° C. for 35 seconds in a quartz tube filled with nitrogen gas to obtain worms of exfoliated graphite flakes.

Example 6

Conductive Web of Filaments from Electro-Spun PAA Fibrils for Anode

Poly (amic acid) (PAA) precursors for spinning were prepared by copolymerizing of pyromellitic dianhydride (Aldrich) and 4,4'-oxydianiline (Aldrich) in a mixed solvent of tetrahydrofurane/methanol (THF/MeOH, 8/2 by weight). The PAA solution was spun into fiber web using an electrostatic spinning apparatus. The apparatus consisted of a 15 kV d.c. power supply equipped with the positively charged capillary from which the polymer solution was extruded, and a negatively charged drum for collecting the fibers. Solvent removal and imidization from PAA were performed concurrently by stepwise heat treatments under air flow at 40° C. for 12 h, 100° C. for 1 h, 250° C. for 2 h, and 350° C. for 1 h. The thermally cured polyimide (PI) web samples were carbonized at 1,000° C. to obtain a sample with an average fibril diameter of 67 nm. Such a web can be used to accommodate sulfur (or lithium polysulfide), vanadium oxide, titanium disulfide, etc., for the cathode and/or as a conductive substrate for an anode active material.

Example 7

Preparation of NGP-based Webs (Webs of NGPs and NGPs+CNFs) for the Anode or Cathode (as a Conductive Nanostructured Support)

The starting natural graphite flakes (original size of 200 mesh, from Huadong Graphite Co., Pingdu, China) was milled to approximately 15 μm. The intercalation and oxidation chemicals used in the present study, including fuming nitric acid (>90%), sulfuric acid (95-98%), potassium chlorate (98%), and hydrochloric acid (37%), were purchased from Sigma-Aldrich and used as received.

A reaction flask containing a magnetic stir bar was charged with sulfuric acid (360 mL) and nitric acid (180 mL) and cooled by immersion in an ice bath. The acid mixture was stirred and allowed to cool for 15 min, and graphite particles (20 g) were added under vigorous stirring to avoid agglomeration. After the graphite particles were well dispersed, potassium chlorate (110 g) was added slowly over 15 min to avoid sudden increases in temperature. The reaction flask was loosely capped to allow evolution of gas from the reaction mixture, which was stirred for 48 hours at room temperature. On completion of the reaction, the mixture was poured into 8 L of deionized water and filtered. The slurry was spray-dried to recover an expandable graphite sample. The dried, expandable graphite sample was quickly placed in a tube furnace preheated to 1,000° C. and allowed to stay inside a quartz tube for approximately 40 seconds to obtain exfoliated graphite worms. The worms were dispersed in water to form a suspension, which was ultrasonicated with a power of 60 watts for 15 minutes to obtain separated NGPs.

Approximately half of the NGP-containing suspension was filtered and dried to obtain several paper-like mats. Vapor grown CNFs were then added to the remaining half to form a suspension containing both NGPs and CNFs (20%), which was dried and made into several paper-like mats. Approximately 5% phenolic resin binder was used to help consolidate the web structures in both samples. Such a web can be as a conductive substrate for an anode active material.

Example 8

Physical Vapor Deposition (PVD) of Sulfur on Mesoporous Graphite Worm Conductive Structures for Li—S Cathodes In a typical procedure, a mesoporous graphite worm structure or a nano-filament web is sealed in a glass tube with the solid sulfur positioned at one end of the glass tube and the web near another end at a temperature of 40-75° C. The sulfur vapor exposure time was typically from several minutes to several hours for a sulfur coating of several nanometers to several microns in thickness. A sulfur coating thickness lower than 100 nm is preferred, but more preferred is a thickness lower than 20 nm, and most preferred is a thickness lower than 10 nm (or even 5 nm). Several lithium metal cells with or without a nano-structured anode were fabricated, wherein a lithium metal foil was used as a source of $Li^+$ ions.

Example 9

Preparation of Graphene-Enabled $Li_xV_3O_8$ Nano-Sheets (as a Cathode Active Material in a Rechargeable Lithium Metal Battery) from $V_2O_5$ and LiOH All chemicals used in this study were analytical grade and were used as received without further purification. $V_2O_5$ (99.6%, Alfa Aesar) and LiOH (99+%, Sigma-Aldrich) were used to prepare the precursor solution. Graphene oxide (GO, 1% w/v obtained in Example 2 above) was used as a structure modifier. First, $V_2O_5$ and LiOH in a stoichiometric V/Li ratio of 1:3 were dissolved in actively stirred deionized water at 50° C. until an aqueous solution of $Li_xV_3O_8$ was formed. Then, GO suspension was added while stirring, and the resulting suspension was atomized and dried in an oven at 160° C. to produce the spherical composite particulates of $GO/Li_xV_3O_8$ nano-sheets. Corresponding $Li_xV_3O_8$ materials were obtained under comparable processing conditions, but without graphene oxide sheets.

An additional set of graphene-enabled $Li_xV_3O_8$ nano-sheet composite particulates was produced from $V_2O_5$ and LiOH under comparable conditions, but was dried under different atomization temperatures, pressures, and gas flow rates to achieve four samples of composite particulates with four different $Li_xV_3O_8$ nano-sheet average thicknesses (4.6 nm, 8.5 nm, 14 nm, and 35 nm). A sample of $Li_xV_3O_8$ sheets/rods with an average thickness/diameter of 76 nm was also obtained without the presence of graphene oxide sheets (but, with the presence of carbon black particles) under the same processing conditions for the graphene-enhanced particulates with a nano-sheet average thickness of 35 nm. It seems that carbon black is not as good a nucleating agent as graphene for the formation of $Li_xV_3O_8$ nano-sheet crystals. The specific capacities and other electrochemical properties of these cathode materials in Li metal cells using lithium foil as a counter electrode and in Li-ion cells using a graphite anode were investigated.

Example 10

Hydrothermal Synthesis of Graphene-Enabled $V_3O_7H_2O$ Nano-Belts from $V_2O_5$ and Graphene Oxide In a typical procedure, 0.015 g of $V_2O_5$ was added into 9 ml of distilled water. A GO-water suspension ($V_2O_5$/GO ratio of 98/2) was poured into the $V_2O_5$ suspension. The resulting mixture was transferred to a 35 ml Teflon-sealed autoclave and stored at 180-200° C. for 24-36 h (different batches), then was air-cooled to room temperature. GO was used as a heterogeneous nucleation agent to promote fast nucleation of larger numbers of nuclei for reduced crystallite sizes (promote nucleation against growth of crystals). The products were washed several times with distilled water, and finally dried at 60° C. in an oven.

A second batch was obtained by spray-drying at 200° C. and heat-treated at 400° C. for 2 hours to obtain particulates of $GO/V_3O_7H_2O$ composite with graphene oxide sheets embracing around these particulates. For comparison purposes, a third batch of $V_3O_7H_2O$ was prepared without using GO (oven dried), a fourth batch was prepared with GO and poly ethylene oxide (1% PEO in water was added to the GO suspension, then spray-dried and heat-treated at 400° C. for 2 hours), and a fifth batch was prepared with PEO (1% in water, but without GO) via spray-drying, followed by heat-treating at 400° C. for 2 hours. Heat treatment of PEO at 400° C. serves to convert PEO to a carbon material. The particulates of $GO/V_3O_7H_2O$ composite were used as a cathode active material in a Li metal cell.

Example 11

Preparation of Electrodes for Li-Ion Cells Featuring a Quasi-Solid Electrolyte

Several dry electrodes containing graphene-enhanced particulates (e.g. comprising lithium cobalt oxide or lithium iron phosphate primary particles embraced by graphene sheets) were prepared by mixing the particulates with a liquid to form a paste without using a binder such as PVDF. The paste was cast onto a surface of a piece of glass, with the liquid medium removed to obtain a dry electrode. Another dry electrode was prepared by directly mixing $LiFePO_4$ primary particles with graphene sheets in an identical liquid to form a paste without using a binder. Again, the paste was then cast to form a dry electrode. The dry electrodes were for the evaluation of the effect of various conductive additives on the electrical conductivity of an electrode.

For comparison purposes, several additional dried electrodes were prepared under exactly identical conditions, and the paste in each case was made to contain the same cathode active particles, but a comparable amount of other conductive additives: multi-walled carbon nano-tubes (CNTs), carbon black (Super-P from Timcal), a CNT/Super-P mixture at an 1/1 ratio, and a GO/Super-P mixture at an 1/1 ratio. Corresponding "wet" electrodes for incorporation in a battery cell were made to contain a PVDF binder. These electrodes were made into full cells containing graphite particles or lithium metal as an anode active material.

The first-cycle discharge capacity data of small full button cells containing lithium metal as an anode active material were obtained. The data show that the battery cells containing graphene-enhanced particulates in the cathode show superior rate capability to that of a carbon black-enhanced cathode. Most importantly, the Li-ion cells having a higher salt concentration in an organic liquid solvent typically exhibit a longer and more stable cycling life, experiencing a significantly lesser extent of capacity decay after a given number of charge/discharge cycles.

It may be further noted that the cathode active material that can be used in the presently invented electrode is not limited to lithium cobalt oxide and lithium iron phosphate. There is no particular limitation on the type of electrode active materials that can be used in a Li-ion cell featuring the presently invented quasi-solid electrolyte.

Example 12

Li-Air Cells with Ionic Liquid Electrolytes Containing Various Salt Concentrations To test the performance of the Li-air battery employing a liquefied gas solvent with different lithium salt concentrations, several pouch cells with dimension of 5 cm×5 cm were built. Porous carbon electrodes were prepared by first preparing ink slurries by dissolving a 90 wt % EC600JD Ketjen black (AkzoNobel) and 5 wt. % Kynar PVDF (Arkema Corporation) in Nmethyl-2-pyrrolidone (NMP). Air electrodes were prepared with a carbon loading of approximately 20.0 mg/cm² by hand-painting the inks onto a carbon cloth (PANEX 35, Zoltek Corporation), which was then dried at 180° C. overnight. The total geometric area of the electrodes was 3.93 cm². The $Li/O_2$ test pouch cells were assembled in an argon-filled glove box. The cell consists of metallic lithium anode and the air electrode as a cathode, prepared as mentioned above. The copper current collector for anode and the aluminum current collector for cathode were used. A Celgard 3401 separator separating the two electrodes was soaked in LiTFSI-Fluoromethane/FPC (6/4) solutions (with different LiTFSI salt concentrations and different electrolyte additives) for a minimum of 24 hours. The cathode was soaked in the oxygen saturated LiTFSI-Fluoromethane/FPC solution for 24 hours and was placed under vacuum for an hour before being used for the cell assembly. The cell was placed in an oxygen filled glove box where oxygen pressure was maintained at 1atm. Cell charge-discharge was carried out with a battery cycler at the current rate of 0.1 mA/cm$^2$ at room temperature. It was found that a higher lithium salt concentration in a liquefied solvent results in a higher round-trip efficiency for cells (61%, 67%, and 74% for x=0.11, 0.22, and 0.32, respectively) and lower capacity decay after a given number of charge/discharge cycles (25%, 8%, and 4.8% for cells with x=0.11, 0.21, and 0.32, respectively, after 100 cycles).

Example 13

Evaluation of Electrochemical Performance of Various Cells

Charge storage capacities were measured periodically and recorded as a function of the number of cycles. The specific discharge capacity herein referred to is the total charge inserted into the cathode during the discharge, per unit mass of the composite cathode (counting the weights of cathode active material, conductive additive or support, binder, and any optional additive combined, but excluding the current collector). The specific charge capacity refers to the amount of charges per unit mass of the composite cathode. The specific energy and specific power values presented in this section are based on the total cell weight. The morphological or micro-structural changes of selected samples after a desired number of repeated charging and recharging cycles were observed using both transmission electron microscopy (TEM) and scanning electron microscopy (SEM).

Figure 8:
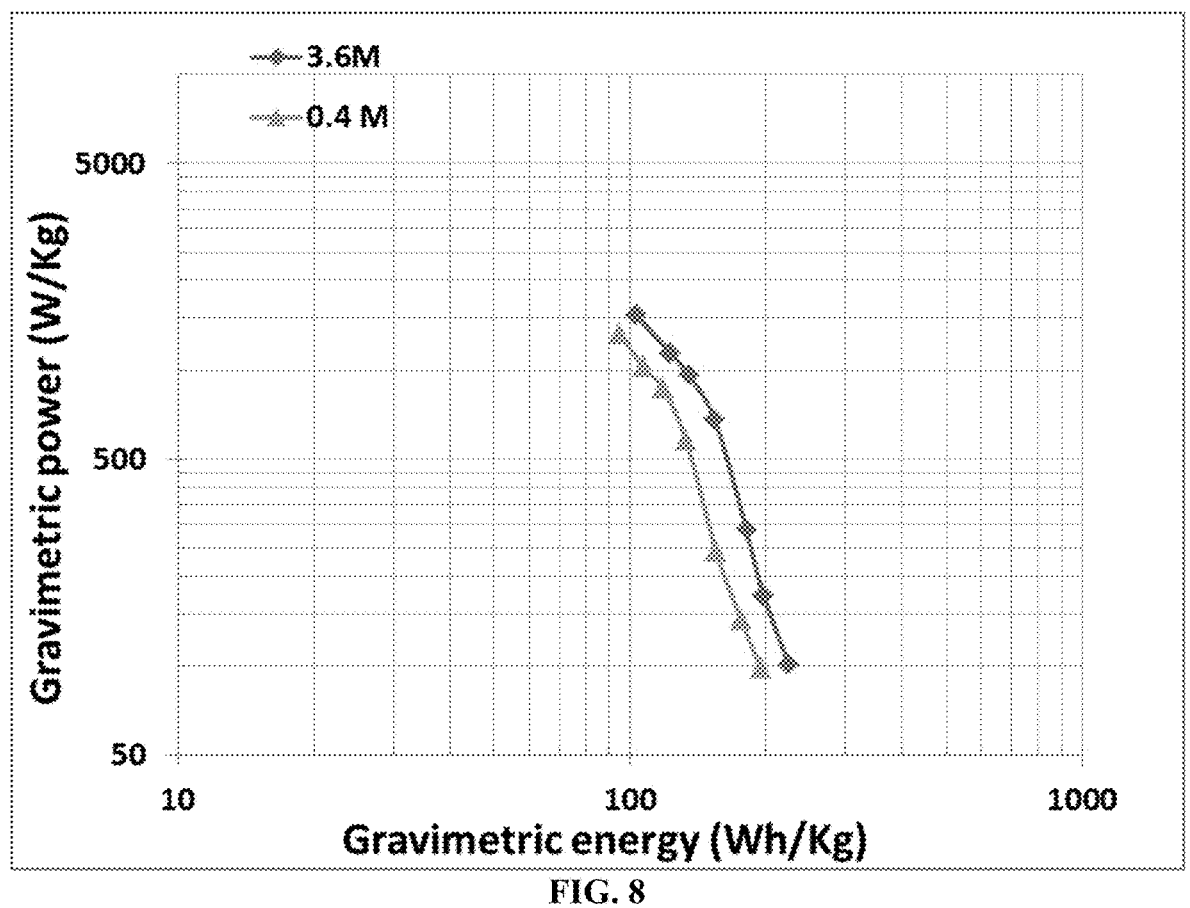
FIG. 8 Ragone plots (cell power density vs. cell energy density) of two lithium-ion cells (spherical graphite anode and NCA cathode), one having a liquefied fluoroethane-based electrolyte having a lithium salt concentration of 0.4 M and the other having a salt concentration of 3.6 M.

As an example, the Ragone plots (cell power density vs. cell energy density) of two lithium-ion cells are shown in FIG. 8. Each cell has a spherical graphite anode and an NCA cathode; but one having a liquefied fluoroethane-based electrolyte having a lithium salt concentration of 0.4 M and the other having a salt concentration of 3.6 M. Quite unexpectedly, the cell having a higher lithium salt concentration delivers not only a high energy density but also a higher power density. A lithium salt concentration in a liquefied gas solvent higher than 1.0 M had not been previously achieved. A concentration as high as 3.6 M would have been considered impossible or undesirable.

As discussed in the Background section, the capacity of a Li—S cell can rapidly decay as charges and discharges are repeated. This is due to the great propensity for sulfur and lithium polysulfide to get dissolved in the electrolyte at the cathode side. Much of the dissolved sulfur or lithium polysulfide could not be re-deposited to the cathode conductive additive/substrate or the cathode current collector during subsequent charges/discharges. Most critically, as time goes on or when charge/discharge cycling continues, some of the dissolved lithium polysulfide species migrate to the anode side and react with Li to form insoluble products and, hence, these species could not return to the cathode. These phenomena lead to continuing decay in the battery capacity.

We proceeded to investigate how the lithium salt concentration would affect the lithium polysulfide dissolution in a liquefied gas solvent, and to determine how concentration changes would impact the thermodynamics and kinetics of the shuttle effect. We immediately encounter some major challenges. First, we did not have a wide range of lithium salt concentrations at our disposal. Most of the lithium salts could not be dissolved in liquefied solvents for more than 0.5 M. Second, we quickly came to realize that the viscosity of many liquefied gas solvents was extremely high at room temperature when the lithium salt reaches 0.5 M. The resulting mixtures look like and behave like a solid. It was next to impossible to use a stirrer to help disperse the solid lithium salt powder in the solvent. Further, a higher solute concentration was generally believed to be undesirable since a higher concentration normally would result in a lower lithium ion conductivity in the electrolyte. This would not be conducive to achieving a higher power density, lower polarization, and higher energy density (at high charge/discharge rates). We almost gave up, but decided to move forward anyway. The research results have been most surprising.

Contrary to the expectations by electrochemists and battery designers that a significantly higher lithium salt concentration could not be produced, we found that a concentration as high as x=0.2-0.6, roughly corresponding to 3-11 M of a lithium salt in a liquefied gas liquid could be achieved, if a highly volatile solvent (such as AN or DOL) is added as a co-solvent first. Once a complete dissolution of a lithium salt in a mixture solvent is attained, we could choose to selectively remove the co-solvent. We were pleasantly surprised to observe that partial or complete removal of the more volatile co-solvent upon complete salt dissolution would not result in crystallization or precipitation of the salt from the organic liquid solvent even though the salt (a solute) was then in a highly supersaturated condition.

We have further defied the expectation of battery chemists and engineers that a higher electrolyte concentration would lead to a lower discharge capacity. Most surprisingly, the Li—S cells contain a higher-concentration electrolyte system exhibit not only a generally higher energy density but also a dramatically more stable cycling behavior and longer cycle life.

Figure 9:
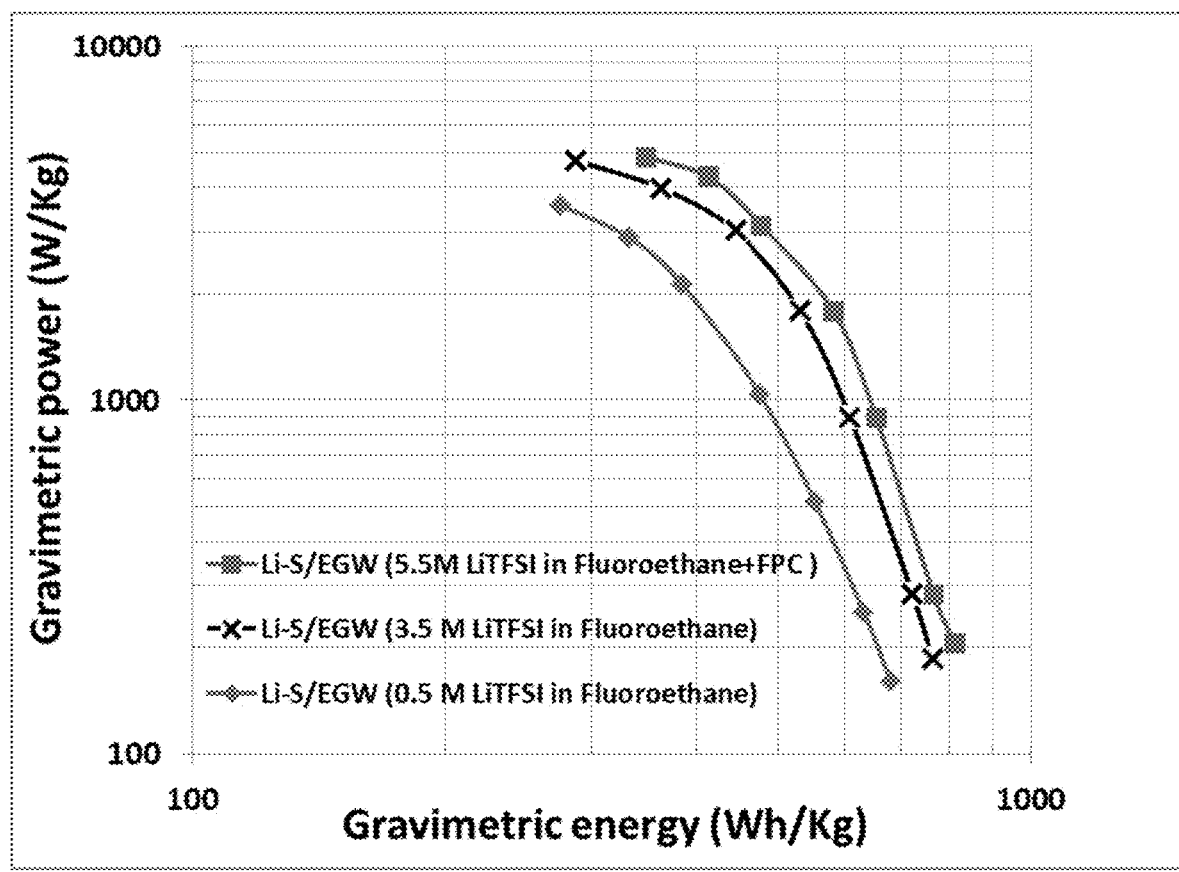
FIG. 9 Ragone plots (cell power density vs. cell energy density) of three Li metal-sulfur cells each having an exfoliated graphite worm-sulfur cathode, but different lithium salt concentrations.

FIG. 9 shows the Ragone plots (cell power density vs. cell energy density) of three Li metal-sulfur cells each having an exfoliated graphite worm-sulfur cathode, but the lithium salt concentrations being 5.5 M (LiTFSI in fluoroethane-FPC mixture), 3.5 M (LiTFSI in fluoroethane), and 0.5 M (LiTFSI in fluoroethane), respectively. The first cell, having a high salt concentration and an electrolyte additive, delivers the highest energy density, as high as 812 Wh/kg. This is 4 times higher than the energy density of a conventional lithium-ion battery.

Figure 10:
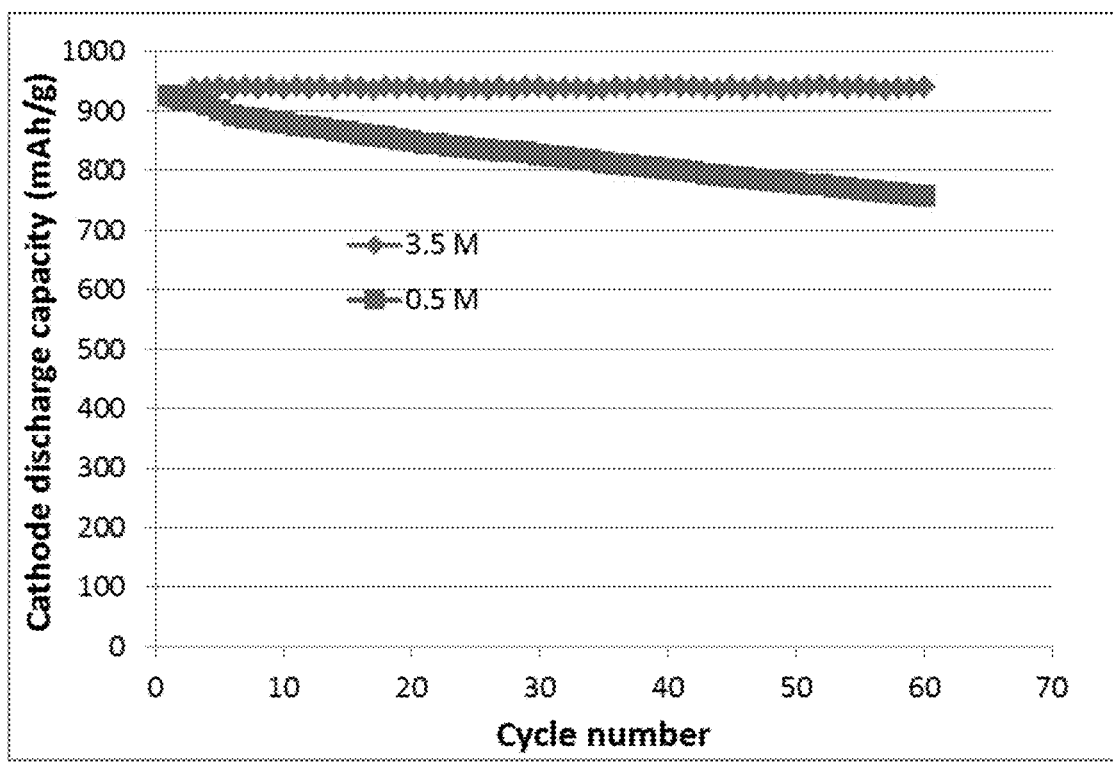
FIG. 10 Cycling performance of two Li metal-sulfur cells, one containing a low-concentration electrolyte (0.5 M) of Li salt in a fluoromethane solvent) and the other containing a high-concentration electrolyte (3.5 M).

Shown in FIG. 10 are the cycling behaviors of two corresponding cells having salt concentrations of 0.5 M and 3.5 M, respectively. The cell featuring a higher salt concentration exhibits a dramatically more stable charge-discharge cycle behavior.

In summary, the present invention provides an innovative, versatile, and surprisingly effective platform materials technology that enables the design and manufacture of superior lithium metal and lithium-ion rechargeable batteries. The lithium cell featuring a high-concentration electrolyte system having a liquefied gas solvent and an optional co-solvent exhibits a stable and safe anode (no dendrite-like feature), high lithium utilization rate, high cathode active material utilization rate, high specific capacity, high specific energy, high power density, little or no shuttling effect, and long cycle life. The presently invented Li—S cells can provide a specific energy greater than 400 Wh/Kg (more typically greater than 600 Wh/Kg, and often greater than 800 Wh/Kg), based on the total cell weight including anode, cathode, electrolyte, separator, and current collector weights combined. This has not been achieved by any prior art approach.

The invention claimed is:

1. A rechargeable lithium cell comprising a cathode having a cathode active material, an anode having an anode active material, an optional ion-permeable membrane disposed between said anode and said cathode, a non-flammable electrolyte containing lithium salt-retained liquefied gas in contact with said cathode and said anode, wherein said electrolyte contains a lithium salt dissolved in or mixed with a liquefied gas solvent having a lithium salt concentration greater than 1.0 M so that said electrolyte exhibits a vapor pressure less than 1 kPa when measured at 20° C., a vapor pressure less than 60% of the vapor pressure of said liquefied gas solvent alone, a flash point at least 20 degrees Celsius higher than a flash point of said liquefied gas solvent alone, a flash point higher than 150° C., or no flash point, wherein said liquefied gas solvent is selected from methane, ethane, propane, ethylene, chloroethylene, or a combination thereof.

2. The rechargeable lithium cell of claim 1, wherein said vapor pressure is less than 0.1 kPa when measured at 20° C.

3. The rechargeable lithium cell of claim 1, wherein said vapor pressure is less than 0.01 kPa when measured at 20° C.

4. The rechargeable lithium cell of claim 1, wherein said lithium salt concentration is from 1.5 M to 14 M.

5. The rechargeable lithium cell of claim 1, wherein said lithium salt concentration is from 2.0 M to 10 M.

6. The rechargeable lithium cell of claim 1, which is a lithium metal secondary cell, a lithium-ion cell, a lithium-sulfur cell, a lithium-ion sulfur cell, a lithium-selenium cell, or a lithium-air cell.

7. The rechargeable lithium cell of claim 1, wherein said electrolyte has a lithium ion transference number greater than 0.4.

8. The rechargeable lithium cell of claim 1, wherein said electrolyte has a lithium ion transference number greater than 0.6.

9. The rechargeable lithium cell of claim 1, wherein said electrolyte has a lithium ion transference number greater than 0.75.

10. The rechargeable lithium cell of claim 1, wherein said electrolyte further contains a liquid solvent mixed with said liquefied gas solvent wherein said liquid solvent is selected from the group consisting of 1,3-dioxolane (DOL), 1,2-dimethoxyethane (DME), tetraethylene glycol dimethylether (TEGDME), poly(ethylene glycol) dimethyl ether (PEGDME), diethylene glycol dibutyl ether (DEGDBE), 2-ethoxyethyl ether (EEE), sulfone, sulfolane, ethylene carbonate (EC), dimethyl carbonate (DMC), methylethyl carbonate (MEC), diethyl carbonate (DEC), ethyl propionate, methyl propionate, propylene carbonate (PC), gamma.-butyrolactone (γ-BL), acetonitrile (AN), ethyl acetate (EA), propyl formate (PF), methyl formate (MF), toluene, xylene, methyl acetate (MA), fluoroethylene carbonate (FEC), vinylene carbonate (VC), allyl ethyl carbonate (AEC), hydrofluoro ether (FIFE), and combinations thereof.

11. The rechargeable lithium cell of claim 1, wherein said electrolyte further contains a liquid solvent mixed with said liquefied gas solvent wherein said liquid solvent is selected from the group consisting of hydrofluoro ether trifluoro propylene carbonate (FPC), methyl nonafluorobutyl ether (MFE), fluoroethylene carbonate (FEC), tris(trimethylsilyl) phosphite (TTSPi), triallyl phosphate (TAP), ethylene sulfate (DTD), 1,3-propane sultone (PS), propene sultone (PES), diethyl carbonate (DEC), alkylsiloxane (Si—O), alkyylsilane (Si—C), liquid oligomeric silaxane (—Si—O—Si—), tetraethylene glycol dimethylether (TEGDME), and combinations thereof.

12. The rechargeable lithium cell of claim 1, wherein said lithium salt is selected from lithium perchlorate ($LiClO_4$), lithium hexafluorophosphate ($LiPF_6$), lithium borofluoride ($LiBF_4$), lithium hexafluoroarsenide ($LiAsF_6$), lithium trifluoro-metasulfonate ($LiCF_3SO_3$), bis-trifluoromethyl sulfonylimide lithium ($LiN(CF_3SO_2)_2$), lithium bis(oxalato)borate (LiBOB), lithium oxalyldifluoroborate ($LiBF_2C_2O_4$), lithium oxalyldifluoroborate ($LiBF_2C_2O_4$), lithium nitrate ($LiNO_3$), Li-Fluoroalkyl-Phosphates ($LiPF_3(CF_2CF_3)_3$), lithium bisperfluoro-ethysulfonylimide (LiBETI), lithium bis(trifluoromethanesulphonyl)imide, lithium bis(fluorosulphonyl)imide, lithium trifluoromethanesulfonimide (LiTFSI), an ionic liquid lithium salt, or a combination thereof.

13. The rechargeable lithium cell of claim 1, wherein a molar fraction or molecular fraction of said lithium salt in said electrolyte is greater than 0.2.

14. The rechargeable lithium cell of claim 1, wherein a molar fraction or molecular fraction of said lithium salt in said electrolyte is greater than 0.3.

15. The rechargeable lithium cell of claim 1, wherein a molar fraction or molecular fraction of said lithium salt in said electrolyte is greater than 0.4.

16. The rechargeable lithium cell of claim 1, wherein said cathode active material is selected from a metal oxide, a metal oxide-free inorganic material, an organic material, a polymeric material, sulfur, lithium polysulfide, selenium, or a combination thereof.

17. The rechargeable lithium cell of claim 16, wherein said inorganic material is selected from a transition metal fluoride, a transition metal chloride, a transition metal dichalcogenide, a transition metal trichalcogenide, or a combination thereof.

18. The rechargeable lithium cell of claim 1, wherein said cathode active material is selected from $FeF_3$, $FeCl_3$, $CuCl_2$, $TiS_2$, $TaS_2$, $MoS_2$, $NbSe_3$, $MnO_2$, $CoO_2$, an iron oxide, a vanadium oxide, or a combination thereof.

19. The rechargeable lithium cell of claim 1, wherein said cathode active material contains a vanadium oxide selected from the group consisting of $VO_2$, $Li_xVO_2$, $V_2O_5$, $Li_xV_2O_5$, $V_3O_8$, $Li_xV_3O_8$, $Li_xV_3O_7$, $V_4O_9$, $Li_xV_4O_9$, $V_6O_{13}$, $Li_xV_6O_{13}$, their doped versions, their derivatives, and combinations thereof, wherein $0.1<x<5$.

20. The rechargeable lithium cell of claim 1, wherein said cathode active material contains a layered compound $LiMO_2$, spinel compound $LiM_2O_4$, olivine compound $LiMPO_4$, silicate compound $Li_2MSiO_4$, Tavorite compound $LiMPO_4F$, borate compound $LiMBO_3$, or a combination thereof, wherein M is a transition metal or a mixture of multiple transition metals.

21. The rechargeable lithium cell of claim 1, wherein said cathode active material contains an inorganic material selected from: (a) bismuth selenide or bismuth telluride, (b) transition metal dichalcogenide or trichalcogenide, (c) sulfide, selenide, or telluride of niobium, zirconium, molybdenum, hafnium, tantalum, tungsten, titanium, cobalt, manganese, iron, nickel, or a transition metal; (d) boron nitride, or (e) a combination thereof.

22. The rechargeable lithium cell of claim 16, wherein said organic material or polymeric material is selected from Poly(anthraquinonyl sulfide) (PAQS), a lithium oxocarbon, 3,4,9,10-perylenetetracarboxylic dianhydride (PTCDA), poly(anthraquinonyl sulfide), pyrene-4,5,9,10-tetraone (PYT), polymer-bound PYT, Quino(triazene), redox-active organic material, Tetracyanoquinodimethane (TCNQ), tetracyanoethylene (TCNE), 2,3,6,7,10,11-hexamethoxytriphenylene (HMTP), poly(5-amino-1,4-dyhydroxy anthraquinone) (PADAQ), phosphazene disulfide polymer ([($NPS_2$)$_3$]n), lithiated 1,4,5,8-naphthalenetetraol formaldehyde polymer, Hexaazatrinaphtylene (HATN), Hexaazatriphenylene hexacarbonitrile (HAT(CN)$_6$), 5-B enzylidene hydantoin, Isatine lithium salt, Pyromellitic diimide lithium salt, tetrahydroxy-p-benzoquinone derivatives (THQLi$_4$), N,N'-diphenyl-2,3,5,6-tetraketopiperazine (PHP), N,N'-diallyl-2,3,5,6-tetraketopiperazine (AP), N,N'-dipropyl-2,3,5,6-tetraketopiperazine (PRP), a thioether polymer, a quinone compound, 1,4-benzoquinone, 5,7,12,14-pentacenetetrone (PT), 5-amino-2,3-dihydro-1,4-dyhydroxy anthraquinone (ADDAQ), 5-amino-1,4-dyhydroxy anthraquinone (ADAM), calixquinone, Li$_4$C$_6$O$_6$, Li$_2$C$_6$O$_6$, Li$_6$C$_6$O$_6$, or a combination thereof.

23. The rechargeable lithium cell of claim 22, wherein said thioether polymer is selected from Poly[methanetetryl-tetra(thiomethylene)] (PMTTM), Poly(2,4-dithiopenta-nylene) (PDTP), a polymer containing Poly(ethene-1,1,2,2-tetrathiol) (PETT) as a main-chain thioether polymers, a side-chain thioether polymer having a main-chain consisting of conjugating aromatic moieties, and having a thioether side chain as a pendant, Poly(2-phenyl-1,3-dithiolane) (PPDT), Poly(1,4-di(1,3-dithiolan-2-yl)benzene) (PDDTB), poly(tetrahydrobenzodithiophene) (PTHBDT), poly[1,2,4, 5-tetrakis(propylthio)benzene] (PTKPTB, or poly[3,4(ethylenedithio)thiophene] (PEDTT).

24. The rechargeable lithium cell of claim 1, wherein said cathode active material contains a phthalocyanine compound selected from copper phthalocyanine, zinc phthalocyanine, tin phthalocyanine, iron phthalocyanine, lead phthalocyanine, nickel phthalocyanine, vanadyl phthalocyanine, fluorochromium phthalocyanine, magnesium phthalocyanine, manganous phthalocyanine, dilithium phthalocyanine, aluminum phthalocyanine chloride, cadmium phthalocyanine, chlorogallium phthalocyanine, cobalt phthalocyanine, silver phthalocyanine, a metal-free phthalocyanine, a chemical derivative thereof, or a combination thereof.

25. The rechargeable lithium cell of claim 1, wherein said electrolyte further contains an ionic liquid solvent.

26. The rechargeable lithium cell of claim 25, wherein said ionic liquid solvent is selected from a room temperature ionic liquid having a cation selected from tetraalkylammonium, di-, tri-, or tetra-alkylimidazolium, alkylpyridinium, dialkyl-pyrrolidinium, dialkylpiperidinium, tetraalkylphosphonium, trialkylsulfonium, or a combination thereof.

27. The rechargeable lithium cell of claim 25, wherein said ionic liquid solvent is selected from a room temperature ionic liquid having an anion selected from BF$_4^-$, B(CN)$_4^-$, CH$_3$BF$_3^-$, CH$_2$CHBF$_3^-$, CF$_3$BF$_3^-$, C$_2$F$_5$BF$_3^-$, n-C$_3$F$_7$BF$_3^-$, n-C$_4$F$_9$BF$_3^-$, PF$_6^-$, CF$_3$CO$_2^-$, CF$_3$SO$_3^-$, N(SO$_2$CF$_3$)$_2^-$, N(COCF$_3$)(SO$_2$CF$_3$)$^-$, N(SO$_2$F)$_2^-$, N(CN)$_2^-$, C(CN)$_3^-$, SCN$^-$, SeCN$^-$, CuCl$_2^-$, AlCl$_4^-$, F(HF)$_{2.3}^-$, or a combination thereof.

28. The rechargeable lithium cell of claim 1 wherein said anode contains an anode active material selected from lithium metal, a lithium metal alloy, a mixture of lithium metal or lithium alloy with a lithium intercalation compound, a lithiated compound, lithiated titanium dioxide, lithium titanate, lithium manganate, a lithium transition metal oxide, Li$_4$Ti$_5$O$_{12}$, or a combination thereof.

29. The rechargeable lithium cell of claim 1 wherein said anode contains an anode active material selected from the group consisting of:
(a) silicon (Si), germanium (Ge), tin (Sn), lead (Pb), antimony (Sb), bismuth (Bi), zinc (Zn), aluminum (Al), nickel (Ni), cobalt (Co), manganese (Mn), titanium (Ti), iron (Fe) and cadmium (Cd), and lithiated versions thereof;
(b) alloys or intermetallic compounds of Si, Ge, Sn, Pb, Sb, Bi, Zn, Al, or Cd with other elements, and lithiated versions thereof, wherein said alloys or compounds are stoichiometric or non-stoichiometric;
(c) oxides, carbides, nitrides, sulfides, phosphides, selenides, and tellurides of Si, Ge, Sn, Pb, Sb, Bi, Zn, Al, Fe, Ni, Co, Ti, Mn, or Cd, and their mixtures or composites, and lithiated versions thereof;
(d) salts and hydroxides of Sn and lithiated versions thereof;
(e) carbon or graphite materials and prelithiated versions thereof; and
combinations thereof.

30. The rechargeable lithium cell of claim 1, which is a Lithium-air cell having a higher round-trip efficiency or higher resistance to capacity decay as compared to a corresponding Lithium-air cell that has an electrolyte salt concentration lower than a molecular fraction of 0.2.

31. A non-flammable electrolyte for a lithium battery, said electrolyte containing lithium salt-retained liquefied gas having a lithium salt dissolved in or mixed with a liquefied gas solvent having a lithium salt concentration greater than 1.0 M so that said electrolyte exhibits a vapor pressure less than 1 kPa when measured at 20° C., a vapor pressure less than 60% of the vapor pressure of said liquefied gas solvent alone, a flash point at least 20 degrees Celsius higher than a flash point of said liquefied gas solvent alone, a flash point higher than 150° C., or no flash point, wherein said liquefied gas solvent is selected from methane, ethane, propane, ethylene, chloroethylene, or a combination thereof.

32. The non-flammable electrolyte of claim 31, wherein said vapor pressure is less than 0.1 kPa when measured at 20° C.

33. The non-flammable electrolyte of claim 31, wherein said vapor pressure is less than 0.01 kPa when measured at 20° C.

34. The non-flammable electrolyte of claim 31, wherein said lithium salt concentration is from 1.5 M to 14 M.

35. The non-flammable electrolyte of claim 31, wherein said lithium salt concentration is from 2.0 M to 10 M.

36. The non-flammable electrolyte of claim 31, wherein said electrolyte has a lithium ion transference number greater than 0.4.

37. The non-flammable electrolyte of claim 31, wherein said electrolyte has a lithium ion transference number greater than 0.6.

38. The non-flammable electrolyte of claim 31, wherein said electrolyte has a lithium ion transference number greater than 0.75.

39. The non-flammable electrolyte of claim 31, wherein said electrolyte further contains a liquid solvent mixed with said liquefied gas solvent wherein said liquid solvent is selected from the group consisting of 1,3-dioxolane (DOL), 1,2-dimethoxyethane (DME), tetraethylene glycol dimethylether (TEGDME), poly(ethylene glycol) dimethyl ether (PEGDME), diethylene glycol dibutyl ether (DEGDBE), 2-ethoxyethyl ether (EEE), sulfone, sulfolane, ethylene carbonate (EC), dimethyl carbonate (DMC), methylethyl carbonate (MEC), diethyl carbonate (DEC), ethyl propionate, methyl propionate, propylene carbonate (PC), gamma.-butyrolactone (γ-BL), acetonitrile (AN), ethyl acetate (EA), propyl formate (PF), methyl formate (MF), toluene, xylene, methyl acetate (MA), fluoroethylene carbonate (FEC), vinylene carbonate (VC), allyl ethyl carbonate (AEC), hydrofluoro ether (HFE), and combinations thereof.

40. The non-flammable electrolyte of claim 31, wherein said electrolyte further contains a liquid solvent mixed with said liquefied gas solvent wherein said liquid solvent is selected from the group consisting of hydrofluoro ether (HFE), trifluoro propylene carbonate (FPC), methyl nonafluorobutyl ether (MFE), fluoroethylene carbonate (FEC), tris(trimethylsilyl)phosphite (TTSPi), triallyl phosphate (TAP), ethylene sulfate (DTD), 1,3-propane sultone (PS), propene sultone (PES), diethyl carbonate (DEC), alkylsiloxane (Si—O), alkyylsilane (Si—C), liquid oligomeric silaxane (—Si—O—Si—), tetraethylene glycol dimethylether (TEGDME), and combinations thereof.

41. The non-flammable electrolyte of claim 31, wherein said lithium salt is selected from lithium perchlorate (LiClO$_4$), lithium hexafluorophosphate (LiPF$_6$), lithium borofluoride (LiBF$_4$), lithium hexafluoroarsenide (LiAsF$_6$), lithium trifluoro-metasulfonate (LiCF$_3$SO$_3$), bis-trifluoromethyl sulfonylimide lithium (LiN(CF$_3$SO$_2$)$_2$), lithium bis(oxalato)borate (LiBOB), lithium oxalyldifluoroborate (LiBF$_2$C$_2$O$_4$), lithium oxalyldifluoroborate (LiBF$_2$C$_2$O$_4$), lithium nitrate (LiNO$_3$), Li-Fluoroalkyl-Phosphates (LiPF$_3$(CF$_2$CF$_3$)$_3$), lithium bisperfluoro-ethysulfonylimide (LiBETI), lithium bis(trifluoromethanesulphonyl)imide, lithium bis(fluorosulphonyl)imide, lithium trifluoromethanesulfonimide (LiTFSI), an ionic liquid lithium salt, or a combination thereof.

* * * * *